(12) United States Patent
Century

(10) Patent No.: US 8,974,771 B2
(45) Date of Patent: Mar. 10, 2015

(54) APPARATUS AND METHOD FOR AEROSOL DELIVERY TO THE LUNGS OR OTHER LOCATIONS OF THE BODY

(75) Inventor: Theodore J. Century, Philadelphia, PA (US)

(73) Assignee: Penn-Century, Inc., Wyndmoor, PA (US)

( * ) Notice: Subject to any disclaimer, the term of this patent is extended or adjusted under 35 U.S.C. 154(b) by 627 days.

(21) Appl. No.: 12/720,341

(22) Filed: Mar. 9, 2010

(65) Prior Publication Data
US 2011/0223116 A1 Sep. 15, 2011

(51) Int. Cl.
*A61K 9/12* (2006.01)
*A61M 11/00* (2006.01)

(52) U.S. Cl.
CPC .............. *A61M 11/00* (2013.01); *A61M 11/006* (2014.02); *A61M 2202/0468* (2013.01); *A61M 2202/30* (2013.01); *A61M 2205/3337* (2013.01); *A61M 2210/1039* (2013.01)
USPC ....................................... 424/45; 128/200.14

(58) Field of Classification Search
None
See application file for complete search history.

(56) References Cited

U.S. PATENT DOCUMENTS

| | | |
|---|---|---|
| 3,947,009 A | 3/1976 | Nelmark |
| 3,984,999 A | 10/1976 | Kopp |
| 4,004,641 A | 1/1977 | Hendrickson |
| 4,005,944 A | 2/1977 | Harris |
| 4,007,915 A | 2/1977 | Chambers |
| 4,224,003 A | 9/1980 | St. Louis |
| 4,227,854 A | 10/1980 | Coffey |
| 4,234,163 A | 11/1980 | Kormendy |
| 4,257,648 A | 3/1981 | Bodine |
| 4,265,129 A | 5/1981 | Bodine |
| 4,278,368 A | 7/1981 | Livesay |
| 4,315,817 A | 2/1982 | Popper |
| 4,375,927 A | 3/1983 | Kniep |
| 4,501,517 A | 2/1985 | Seyle |
| 4,585,042 A | 4/1986 | Hutson |
| 4,603,718 A | 8/1986 | Hutson |
| 4,616,716 A | 10/1986 | Bouplon |
| 4,698,926 A | 10/1987 | Caplis et al. |
| 4,706,762 A | 11/1987 | Harms et al. |
| 4,776,442 A | 10/1988 | Young |
| 4,795,552 A | 1/1989 | Yun et al. |
| 4,819,810 A | 4/1989 | Hoppe |
| 4,949,715 A | 8/1990 | Brugger |
| 5,117,925 A | 6/1992 | White |
| 5,190,645 A | 3/1993 | Burgess |
| 5,220,845 A | 6/1993 | Anderson |
| 5,249,892 A | 10/1993 | Fox et al. |
| 5,257,667 A | 11/1993 | Sano et al. |
| 5,261,331 A | 11/1993 | Baudin |
| 5,285,890 A | 2/1994 | Stearns |
| 5,335,779 A | 8/1994 | Negrete |
| 5,409,070 A | 4/1995 | Roussy |
| 5,476,421 A | 12/1995 | Moore et al. |
| 5,478,159 A | 12/1995 | Schneider et al. |
| 5,526,590 A | 6/1996 | Palm et al. |
| 5,579,758 A | 12/1996 | Century |
| 5,588,916 A | 12/1996 | Moore |
| 5,594,987 A | 1/1997 | Century |
| 5,606,789 A | 3/1997 | Century |
| 5,713,418 A | 2/1998 | Warren et al. |
| 5,787,786 A | 8/1998 | Zeuner |
| 5,964,223 A | 10/1999 | Baran |
| 5,964,306 A | 10/1999 | Barbera |
| 5,988,297 A | 11/1999 | Zimmerman et al. |
| 6,016,800 A | 1/2000 | Century |
| 6,029,657 A | 2/2000 | Century |
| 6,041,775 A | 3/2000 | Century |
| 6,079,413 A | 6/2000 | Baran |
| 6,079,969 A | 6/2000 | Sanders |
| 6,106,495 A | 8/2000 | Scott |
| 6,123,070 A | 9/2000 | Bruna et al. |
| 6,203,519 B1 | 3/2001 | Fagerstrom et al. |
| 6,227,195 B1 | 5/2001 | Gonda |
| 6,269,810 B1 * | 8/2001 | Brooker et al. ........... 128/203.12 |
| 6,398,266 B1 | 6/2002 | Crump |
| 6,443,152 B1 | 9/2002 | Lockhart et al. |
| 6,463,658 B1 | 10/2002 | Larsson |
| D466,607 S | 12/2002 | Cise et al. |
| D473,941 S | 4/2003 | Cise et al. |
| D476,731 S | 7/2003 | Cise et al. |
| 6,588,987 B1 | 7/2003 | Degen et al. |
| 6,606,992 B1 | 8/2003 | Schuler et al. |
| 6,609,576 B1 | 8/2003 | Hubbard |
| 6,644,309 B2 | 11/2003 | Casper et al. |
| 6,655,379 B2 | 12/2003 | Clark et al. |
| D486,909 S | 2/2004 | Cise et al. |
| 6,691,704 B2 | 2/2004 | Bibi et al. |
| 6,715,563 B2 | 4/2004 | Hubbard |
| 6,722,364 B2 | 4/2004 | Connelly et al. |
| 6,763,948 B2 | 7/2004 | Ballman et al. |
| 6,792,940 B2 | 9/2004 | Ganan-Calvo |
| 6,830,155 B2 | 12/2004 | Trench et al. |
| 6,854,460 B1 | 2/2005 | Shofner, II et al. |
| 6,915,802 B1 | 7/2005 | Anderson et al. |
| 6,929,005 B2 | 8/2005 | Sullivan et al. |
| 6,943,267 B1 | 9/2005 | Hengge et al. |
| 6,962,564 B2 | 11/2005 | Hickle |
| 7,051,734 B2 | 5/2006 | Casper et al. |
| 7,059,319 B2 | 6/2006 | Ganan-Calvo |
| 7,059,321 B2 | 6/2006 | Ganan-Calvo |

(Continued)

OTHER PUBLICATIONS

Penn-Century™, "Expanding the Reach of Aerosol Drug Delivery," Penn-Century™, containing Penn-Century™ MICROSPRAYER® Aerosolizer Models 1A-1C and 1A-1B, Penn-Century™ pamphlet, no date, 9 pages.

*Primary Examiner* — Susan Tran
*Assistant Examiner* — Jessica Worsham
(74) *Attorney, Agent, or Firm* — Saul Ewing LLP

(57) ABSTRACT

This disclosure relates to an apparatus useful for the delivery of aerosols, such as those containing drugs, to the lungs or other locations in the body. The disclosure also relates to methods of administering an aerosol to the lungs or other locations in the body of a patient.

24 Claims, 7 Drawing Sheets

(56) References Cited

U.S. PATENT DOCUMENTS

| | | | |
|---|---|---|---|
| 7,059,802 B1 | 6/2006 | Geier et al. |
| 7,080,958 B1 | 7/2006 | Morris |
| 7,114,371 B2 | 10/2006 | Swanson et al. |
| 7,134,513 B1 | 11/2006 | Randall et al. |
| 7,185,651 B2 | 3/2007 | Alston et al. |
| 7,246,617 B1 | 7/2007 | Harmer et al. |
| 7,255,406 B1 | 8/2007 | Huck et al. |
| 7,270,127 B2 | 9/2007 | Lockhart et al. |
| 7,296,566 B2 | 11/2007 | Alchas |
| 7,320,319 B2 | 1/2008 | Bonutti |
| 7,334,580 B2 | 2/2008 | Smaldone et al. |
| 7,341,059 B2 | 3/2008 | Moody et al. |
| 7,360,541 B2 | 4/2008 | Dhuper et al. |
| 7,402,137 B2 | 7/2008 | Lomask et al. |
| 7,473,219 B1 | 1/2009 | Glenn |
| 7,588,062 B1 | 9/2009 | Green |
| 7,588,169 B1 | 9/2009 | Green et al. |
| 7,598,429 B2 | 10/2009 | Heard et al. |
| 7,601,893 B2 | 10/2009 | Reuber et al. |
| 7,635,800 B2 | 12/2009 | Ratcliffe et al. |
| 7,641,906 B2 | 1/2010 | Gu |
| 7,647,988 B2 | 1/2010 | Roussy |
| 7,654,975 B2 | 2/2010 | Mantell |
| 7,663,025 B2 | 2/2010 | Heard et al. |
| 7,678,087 B2 | 3/2010 | Penner et al. |
| 8,245,708 B2 | 8/2012 | Smaldone et al. |
| 2003/0150462 A1 | 8/2003 | Dhuper et al. |
| 2003/0187408 A1 | 10/2003 | Marx |
| 2004/0163646 A1 | 8/2004 | Schuster et al. |
| 2004/0235130 A1 | 11/2004 | Brandsch |
| 2005/0042170 A1 | 2/2005 | Jiang et al. |
| 2005/0249822 A1 | 11/2005 | Pilkiewicz et al. |
| 2006/0198901 A9 | 9/2006 | Holloway, Jr. et al. |
| 2007/0122349 A1* | 5/2007 | Wachtel et al. ............ 424/45 |
| 2007/0123422 A1 | 5/2007 | Steffen |
| 2007/0141058 A1 | 6/2007 | Iliich et al. |
| 2007/0281025 A1 | 12/2007 | Hughes et al. |
| 2008/0026029 A1 | 1/2008 | Wellinghoff et al. |
| 2008/0038301 A1 | 2/2008 | Ueda |
| 2008/0260857 A1 | 10/2008 | Pomytkin et al. |
| 2008/0262650 A1 | 10/2008 | Dorendorf et al. |
| 2008/0299220 A1 | 12/2008 | Tamarkin et al. |
| 2008/0311058 A1 | 12/2008 | Lou et al. |
| 2009/0017129 A1 | 1/2009 | Ma'or et al. |
| 2010/0021464 A1 | 1/2010 | Archambeau et al. |
| 2010/0043790 A1 | 2/2010 | Tatarek |
| 2011/0270126 A1 | 11/2011 | Gunday et al. |

* cited by examiner

APPARATUS AND METHOD FOR AEROSOL DELIVERY TO THE LUNGS OR OTHER LOCATIONS OF THE BODY

TECHNICAL FIELD

This disclosure relates to an apparatus useful for the delivery of aerosols, such as those containing pharmaceutically and/or biologically active agents (e.g., drugs), to the lungs or other locations in the body. The disclosure also relates to methods of using the disclosed apparatus for administering an aerosol to the lungs or other locations in the body of a patient.

BACKGROUND

Aerosols represent an important delivery form for the administration of pharmaceutically active agents to patients. Typically, aerosols are homogenous colloidal mixtures that comprise a dispersed phase and a continuous, gaseous medium.

One example of an aerosol is a liquid aerosol in which the dispersed phase is a liquid and the continuous medium is a gas. Liquid aerosols are an important delivery form for the administration of pharmaceutically active agents to patients. Liquid aerosols can be used to deliver diverse categories of pharmaceutically active agents. These pharmaceutically active agents can include small molecules such as cancer treating chemotherapeutic agents, peptide chains such as therapeutic antibodies or vaccine antigens and nucleic acids, such as DNA or siRNA, for gene therapy.

Epithelial tissue lining the lungs, as well as other organs and body cavities, is a very important target tissue for the delivery of pharmaceutical compositions to patients. In fact, the delivery of aerosols to different parts of the respiratory tract, such as the airways and alveoli, may be used to treat a variety of different conditions. These conditions include lung cancer, asthma, bronchitis, bronchiectasis, pneumonia, infectious diseases, tuberculosis, influenza, inflammatory disease, chronic obstructive pulmonary disease, cystic fibrosis, respiratory distress syndrome, Parkinson's disease, diabetes, osteoporosis and systemic diseases such as cardiopulmonary hypertension. The targeted delivery of aerosols containing pharmaceutically active agents also helps avoid side effects associated with the oral, or parenteral, administration of some pharmaceutically active agents.

A significant limitation in the use of aerosols in treating patients has been that only small volumes of aerosols can be delivered to target tissues, such as the lungs, using existing technologies. Aerosols generated by jet, thermal, or ultrasonic methods and delivered by inhalation are relatively slow, highly inefficient and imprecise. They depend upon the ability of the patient to respire a clinically effective dose, that is being directed at the patient's nose and mouth at high speed in relatively low concentrations. If the patient is a newborn with impaired respiratory function, is unconscious or is too physically impaired by disease, the ability to achieve a sufficient concentration in the lungs may not be feasible by inhalation alone. This can have additional consequences. For example, if antibiotics are administered as inhaled therapies via a nebulizer in insufficient concentrations to fully overcome the disease, this may expose the patient to greater likelihood of antibiotic resistance. Aerosol generating methods that depend on compressed air or propellants to generate particles in the 1-5 micron size range which are small enough to be respirable by the patient from outside the body are typically moving at high momentum which can force as much as 95% of the dose against the back of the throat, where it may be coughed up or swallowed. Current inhalation therapies do not permit targeted local/regional drug administration to a lobe or lesion within the lung. They do not protect the nose, mouth, throat, trachea or other sensitive tissues in the respiratory tract from exposure to drugs that may be hazardous or harmful to healthy tissue if respired, such as aerosolized chemotherapy. The small particles size produced by inhalation therapy methods are also more likely to be exhaled by the patient, contaminating the environment and creating potential hazards for caregivers. In addition, these technologies that depend on heat, or propellants, can affect the efficacy and viability of many therapeutic formulations and alter the pharmaceutically and/or biologically active agents that are being delivered. Such inhalation technologies are also incompatible with the administration of drugs in aerosol form to many other target tissues and organs.

Thus, a need exists for apparatuses and methods that may be used to administer efficiently and precisely deliver aerosols to target tissues, and organs, such as the lungs.

SUMMARY

We provide an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve having a delivery outlet and a release outlet; an aerosolizer in fluid communication with the delivery outlet; and a restrictor in fluid communication with the release outlet.

One aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve having a delivery outlet and a release outlet; an aerosolizer in fluid communication with the delivery outlet; and a restrictor in fluid communication with the release outlet.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve containing a fluid at high pressure and having a delivery outlet and a release outlet; a controller connected to the switching valve; a flexible connector in fluid communication with the delivery outlet; an aerosolizer in fluid communication with the flexible connector; and a restrictor in fluid communication with the release outlet.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; and an aerosolizer in fluid communication with the high pressure pump outlet.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a controller connected to the high pressure pump; a flexible connector in fluid communication with the high pressure pump outlet; and an aerosolizer in fluid communication with the flexible connector.

Another aspect of the disclosure is an apparatus comprising a reservoir in fluid communication with an outlet channel; a low pressure pump inlet in fluid communication with the outlet channel; a high pressure pump in fluid communication with the low pressure pump inlet, a high pressure pump outlet in fluid communication with the high pressure pump; a switching valve in fluid communication with the high pressure pump outlet, said switching valve containing a fluid at high pressure and having a delivery outlet and a release outlet; a controller connected to the switching valve; a flexible connector in fluid communication with the delivery outlet; an aerosolizer in fluid communication with the flexible connector; and a restrictor in fluid communication with the release outlet.

Another aspect of the disclosure is a method of administering an aerosol to a patient comprising providing an apparatus of the disclosure; placing the aerosolizer adjacent to a target tissue in a patient; and operating the apparatus to produce an aerosol; whereby an aerosol is administered to the patient.

Another aspect of the disclosure is a method of administering a chemotherapeutic aerosol to the lungs of a patient comprising providing the apparatus of the disclosure in which the reservoir contains a chemotherapeutic agent placing the aerosolizer adjacent to a target tissue in the lungs of a patient; and operating the apparatus to produce a chemotherapeutic aerosol; whereby a chemotherapeutic aerosol is administered to the lungs of the patient.

Another aspect of the disclosure is an apparatus comprising a reservoir in fluid communication with a pressure generator; a flexible connection in fluid communication with the pressure generator; and an aerosolizer in fluid communication with the pressure generator.

The disclosure also provides methods of administering an aerosol to a patient by operating the disclosed apparatus to produce an aerosol.

BRIEF DESCRIPTION OF THE DRAWINGS

FIG. 2 shows, from a frontal perspective, one example of a switching valve of an apparatus of the disclosure.

FIG. 3 shows, from a side perspective, an exploded view of one example of an aerosolizer of an apparatus of the disclosure.

FIG. 4 shows, from a side perspective, a cut away view of one example of an aerosolizer of an apparatus of the disclosure.

Figures 8, 9, 10:
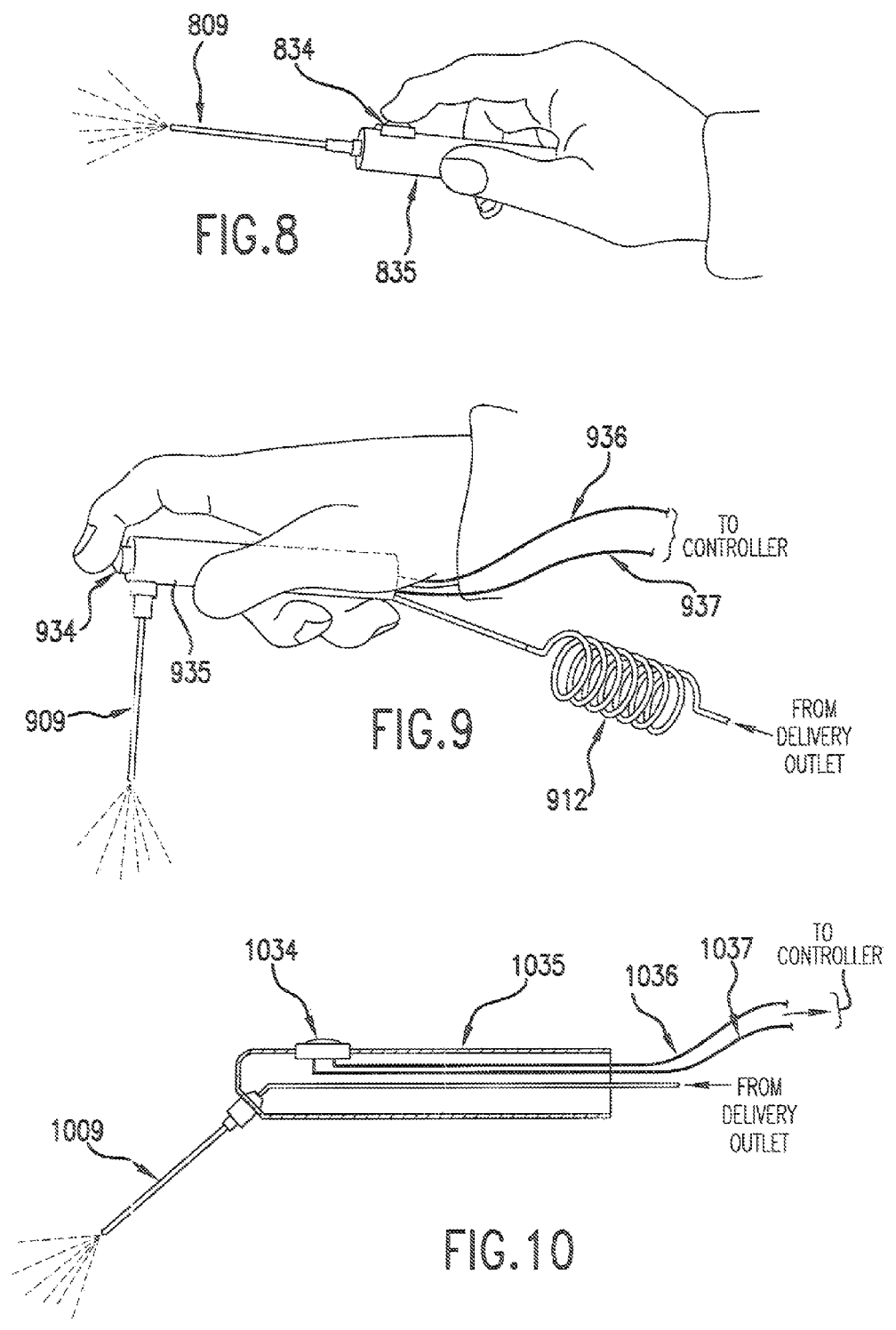

FIG. 8 shows, from a side perspective, one embodiment of a controller of an apparatus of the disclosure.

FIG. 9 shows, from a side perspective, one embodiment of a controller of an apparatus of the disclosure.

FIG. 10 shows, from a side perspective, a cross-section through a long axis of one embodiment of a controller of an apparatus of the disclosure.

DETAILED DESCRIPTION

Figure 1:
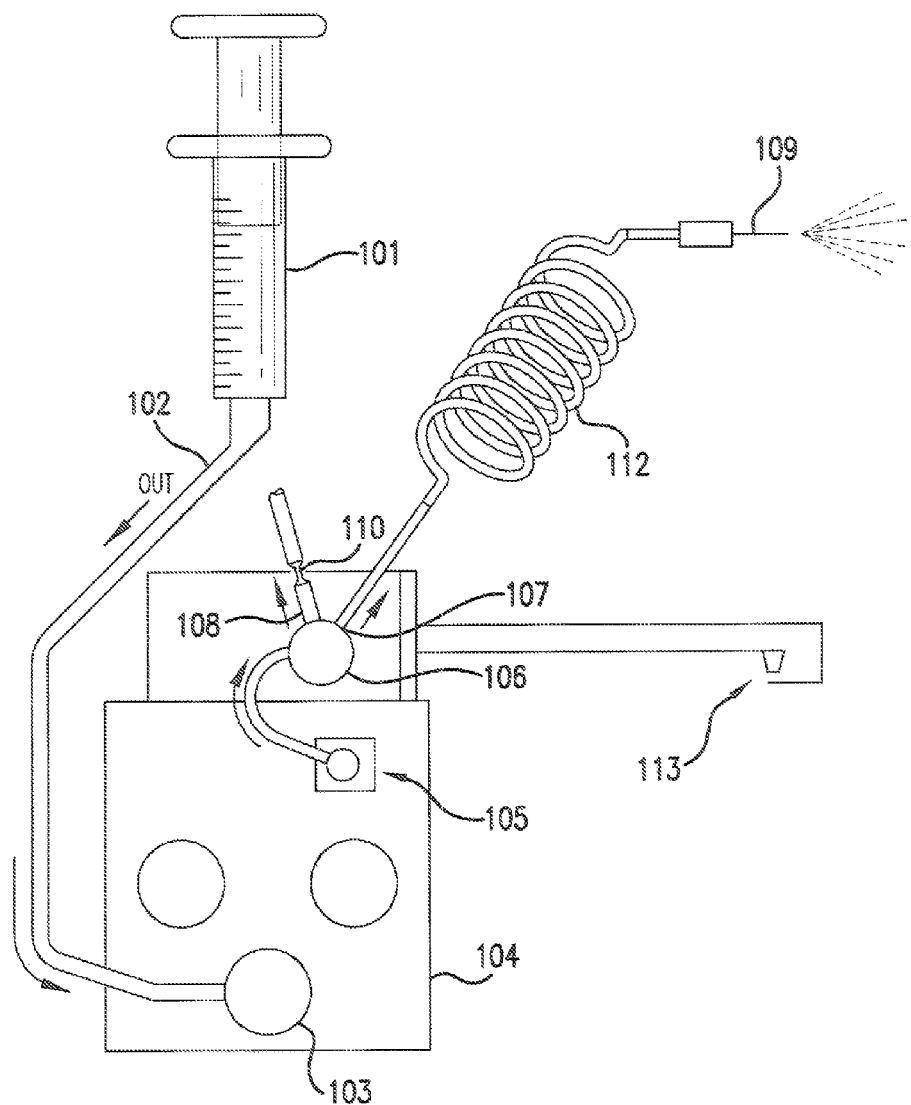
FIG. 1 shows, from a frontal perspective, one embodiment of an apparatus of the disclosure.

It will be appreciated that the following description is intended to provide details concerning specific representative aspects of the disclosure. It will also be appreciated that a wide variety of equivalents may be substituted for the specified elements of the methods described herein without departing from the spirit and scope of this disclosure as described in the appended claims. Additionally, all publications, including but not limited to patents and patent applications, cited in this disclosure are herein incorporated by reference as though fully set forth. Ranges identified herein are intended to include the values defining the upper and lower limits of a recited range, all discrete values within the range and any discrete sub-range within the range.

The term "reservoir" as used herein includes any container able to hold a volume of a fluid. A reservoir may be a vessel of any configuration such as, for example, a syringe, bottle, bladder, jar, vial or canister. A reservoir may also be sealed and enclose an interior space that is, partially or completely, inaccessible to the surrounding external environment.

The term "fluid" as used herein includes any substance that continually deforms, or flows, under an applied shear stress. A fluid may comprise a gas or liquid and may also contain solids (e.g., slurries, suspensions, etc.).

The term "fluid communication" as used herein means that fluid can be transferred, either directly or indirectly, between at least two components of an apparatus. This term also describes a physical relationship between components. For example, a first component may be placed in fluid communication with a second component by a connecting conduit, such as a pipe joining each component so that a volume of fluid can be transferred from the first component to the second component or vice versa.

The term "outlet channel" as used herein includes any opening in a reservoir through which a fluid can be transferred, directly or indirectly, to a low pressure pump inlet.

The term "low pressure pump inlet" as used herein includes any opening on a high pressure pump through which a fluid, at a pressure lower than the fluid pressure generated by the pump, can be transferred, directly or indirectly, to the high pressure pump.

The term "high pressure pump" as used herein includes any device able to move a fluid and to produce a fluid exerting a pressure of at least about 300 pounds per square inch. Examples of high pressure pumps include direct lift, displacement, velocity, buoyancy and gravity pumps. High pressure pumps can also produce fluids exerting pressures of at least about 400 pounds per square inch, of at least about 2,500 pounds per square inch, of at least about 3,000 pounds per square inch, of at least about 3,500 pounds per square inch, of at least about 6,000 pounds per square inch, of at least about 15,000 pounds per square inch, of at least about 20,000 pounds per square inch, and of at least about 300 pounds per square inch to about 20,000 pounds per square inch or more.

The term "high pressure pump outlet" as used herein includes any opening on a high pressure pump through which a fluid can be transferred, directly or indirectly, to a switching valve or an aerosolizer.

The term "pressure generator" as used herein includes any structure that generates a pressure differential sufficient to move a fluid.

The term "switching valve" as used herein includes any valve comprising at least one delivery outlet and at least one release outlet in fluid communication with a high pressure pump outlet, so that the valve can be configured to transfer a fluid though either a delivery outlet or a release outlet. A switching valve may also comprise multiple valves that can be configured to transfer a fluid through either a delivery outlet or a release outlet.

The term "delivery outlet" as used herein includes any opening on a switching valve through which a fluid can be transferred, directly or indirectly, to an aerosolizer. This means a delivery outlet is in fluid communication with an aerosolizer which produces an aerosol to be delivered.

The term "release outlet" as used herein includes any opening on a switching valve through which a fluid can be transferred, directly or indirectly, to a restrictor.

The term "aerosolizer" as used herein includes any structure through which a liquid, such as liquid droplets, or a solid, such as a particulate, is released and entrained in a gas to produce an aerosol in which the dispersed phase comprises a liquid, or a solid, and the continuous medium comprises a gas. An aerosolizer may comprise an orifice through which liquid droplets are released and entrained in a gas to produce a liquid aerosol. An aerosolizer may also comprise an orifice through which a gas passes into a fluid to produce a liquid aerosol. An aerosolizer may comprise an orifice through which solids, such as particulates, are released and entrained in a gas to produce a solid aerosol. An aerosolizer may also comprise an orifice through which a gas passes into a solid, such as a collection or particulates or a friable substance, to produce a solid aerosol.

The term "restrictor" as used herein includes any structure that has a inlet side, an outlet side and a structure that constrains the flow of a fluid to maintain a high pressure fluid on the inlet side and produce a low pressure fluid on the outlet side.

The term "high pressure fluid" as used herein includes without limitation any liquid exerting a pressure of at least about 300 pounds per square inch. A high pressure fluid can also exert pressures of at least about 400 pounds per square inch, of at least about 2,500 pounds per square inch, of at least about 3,000 pounds per square inch, of at least about 3,500 pounds per square inch and of at least 300 pounds per square inch to about 3,500 pounds per square inch.

The term "controller" as used herein includes any device that affects the operation of a pump or switching valve and regulates whether the switching valve is configured to transfer a fluid though either a delivery outlet or a release outlet.

The term "release outlet return" as used herein includes any opening on the reservoir through which a fluid can be transferred, directly or indirectly, into the reservoir.

The term "target tissue" as used herein includes any aggregate of cells forming a structure of an animal to which an aerosol is to be administered.

The term "patient" as used herein includes an animal belonging to any genus to which administration of an aerosol is indicated. One example of such a subject is a human such as a human patient.

The term "aerosol" as used herein means an aerosol in which the dispersed phase comprises a liquid or solid and the continuous medium comprises a gas. A liquid aerosol in which the dispersed phase comprises a liquid and the continuous medium comprises a gas is one example of an aerosol. A solid aerosol in which the dispersed phase comprises a solid, such as a particulate, and the continuous medium comprises a gas is another example of an aerosol.

The term "chemotherapeutic agent" as used herein includes pharmaceutical agents used to treat or prevent cancer.

The term "chemotherapeutic aerosol" as used herein means an aerosol which comprises a chemotherapeutic agent.

One aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve having a delivery outlet and a release outlet; an aerosolizer in fluid communication with the delivery outlet; and a restrictor in fluid communication with the release outlet.

In the apparatus of the disclosure the reservoir may be a syringe, or other vessel such as a canister or flexible bladder, with walls defining an interior space that can contain a fluid that is a liquid or gas. The reservoir may also comprise a vessel such as a vial containing a fluid sealed with a septum that is placed in fluid communication with an outlet channel by piercing, or removing, a portion of the septum. The septum may comprise any appropriate material such as polymers, alloys and the like, that may be pierced with a piercing structure, such as a needle, and maintains a seal with the piercing structure such that fluid in the reservoir does not leak past the sides of the piercing structure. For example, the reservoir may be a glass vial having a volume of 20 mL with a rubber septum affixed to the vial with a metal seal. Those of ordinary skill in the art will recognize other reservoir configurations suitable for use in the apparatus of the disclosure.

Figure 11:
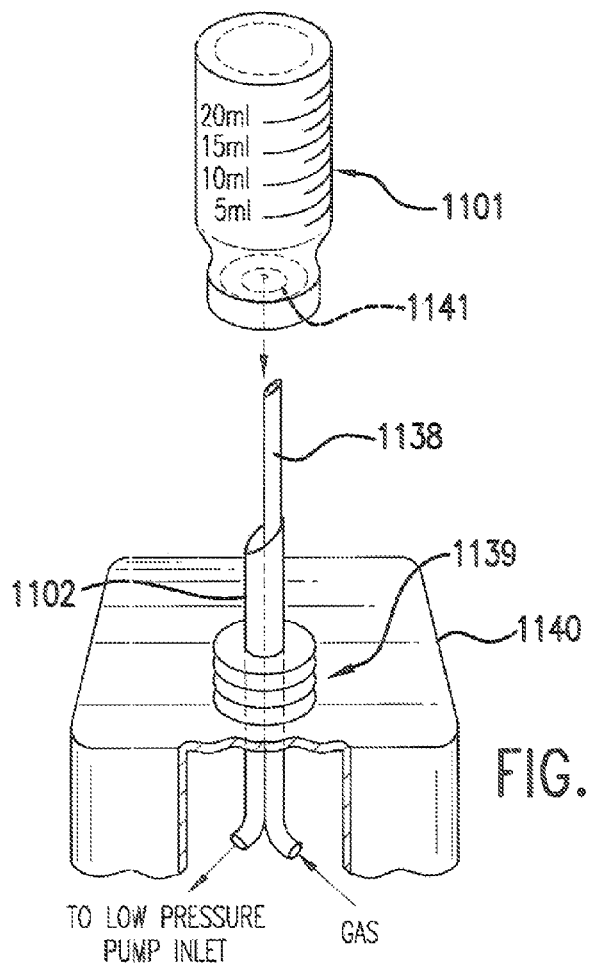
FIG. 11 shows, from a side perspective, one embodiment of a reservoir of an apparatus of the disclosure.

As described above, a vial with a septum may be used as a reservoir. Such a reservoir may be conveniently filled with a fluid sample, sterilized, and stored before the production and administration of an aerosol. Such a vial may have volume graduations, as shown in FIG. 11, so that fluid sample delivery can be monitored. Fluid in the vial can be placed in fluid communication with the apparatus by holding the vial vertically, then inverting the vial and pushing the vial down onto one or more needles, or other structures, which form an outlet channel or gas inlet through a septum in the vial. The vial is pushed onto the needles until the openings of both the inlet and outlet channels are inside the vial and fluid in the vial is able to enter the needle forming the outlet channel. When a pump of the apparatus is activated, fluid is withdrawn from the vial and a gas, such as air, can enter the vial to passively compensate for any changes in fluid volume. This is necessary because the vial is a closed system and the air vent permits ambient pressure to be maintained inside this reservoir. The gas inlet may also comprise a filter to avoid contamination of the reservoir and any fluid therein and a slight positive pressure may also be maintained in the gas inlet to keep fluid out of the gas inlet.

Alternatively, fluid in a vial, or other reservoir, comprising a septum can be placed in fluid communication with the apparatus when the vial comprising a septum is in the vertical orientation by pushing the vial up onto one or more needles, or other structures, downwardly through the septum such that the needle forming the outlet channel passes through a headspace containing a gas in the vial and into the fluid below and the needle forming the gas inlet channel remains in the headspace, without entering the fluid below, to prevent fluid from entering the gas inlet. Thus, those of ordinary skill in the art will recognize that in the apparatus of the disclosure a reservoir may be placed in a variety of orientations.

In some embodiments, the gas inlet and the outlet channel can be adjustable to accommodate different fluid volumes or headspace volumes in different size vials or changes in those volumes as the apparatus is operated. For example, the gas inlet, or the outlet channel, can be axially moveable, relative to an axis passing through the reservoir, to accommodate different fluid volumes or headspace volumes in different size vials or changes in those volumes as the apparatus is operated After delivery of the desired amount of fluid to the apparatus, the vial may be removed from the apparatus and discarded. A typical protocol for delivery of a therapeutic agent might include a post-delivery flush of the apparatus of the disclosure with distilled water, saline, or alcohol. Vials, or other reservoir structures, containing sterile samples of these fluids can be prepared ahead of time to facilitate the delivery of these fluids to the apparatus. After delivery and cleaning, a safety cap may be placed over one or more of the needles, or other structures, forming the outlet channel or gas inlet to control contamination of the apparatus when it is not in use. The safety cap may be fastened in place over such needles, or other outlet channels and/or gas inlets, using any appropriate fastener structure such as clips, threads, snaps and the like. Thus, in some embodiments the apparatus of the disclosure may lack a reservoir. Additionally, in some embodiments the apparatus of the disclosure can comprise a platform which supports at least one of the outlet channel and the gas inlet, a fastener on the platform such as threads and, optionally, a safety cap that can be attached to the fastener when a reservoir is absent. Alternatively, the platform can support the reservoir, such as a vial with a septum, placed in a vertical orientation so that a headspace containing a gas is adjacent to the septum and located above a fluid in the reservoir.

Figure 12:
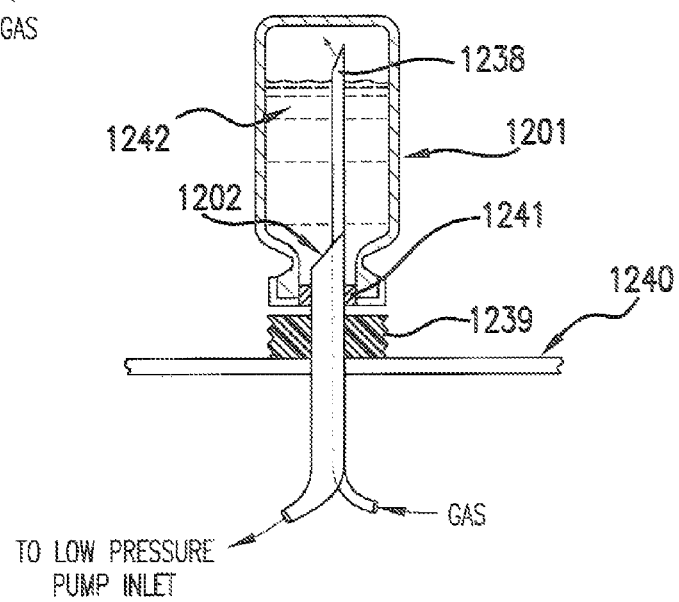
FIG. 12 shows, from a side perspective, a cross-section through one embodiment of a reservoir of an apparatus of the disclosure.

FIG. 11 and FIG. 12 show, from side perspectives, one embodiment of a reservoir of an apparatus of the disclosure. In this embodiment, the reservoir 1101, 1201 may comprise a graduated vial sealed with a septum 1141, 1241. The septum 1141, 1241 can be pierced with a needle comprising an outlet channel 1102, 1202 through which a fluid 1242 in the reservoir 1101, 1201 may be transferred to a low pressure pump inlet and comprising a gas inlet 1138, 1238 to admit a gas, such as air, into the reservoir to compensate for the volume fluid transferred out of the reservoir 1101, 1201. In this embodiment the apparatus may comprise a platform 1140, 1240, such as an apparatus housing, which can support the reservoir 1101, 1201 and may comprise threads 1139, 1239 or another suitable structure for securing a safety cap over the outlet channel 1102, 1202 and gas inlet 1138, 1238. Although FIG. 11 and FIG. 12 show the tubes forming the outlet channel 1102, 1202 and gas inlet channel 1138, 1238 placed coaxially, the two tubes could also be separated, provided that the distance between them is sufficient to for the septum 1141, 1241 to form a complete seal around each tube.

In the apparatus of the disclosure the outlet channel may be any opening in the reservoir though which a fluid can exit the reservoir. It is preferred that the outlet be located at the bottom of a vertically positioned reservoir so that fluid transferred from the reservoir will not contain bubbles that could interfere with the formation of aerosols. The outlet may also be placed at other appropriate locations on the reservoir and fluid transferred from the reservoir can enter a degasser where any bubbles or dissolved gases are removed. The DEGASSEX™ Solvent Degasser having part number EHO-5847 and described as a 4-Channel DEGASSEX™ DG-4400 from PHENOMENEX™ (Torrance, Calif.) is one example of such a degasser. Those of ordinary skill in the art will recognize other appropriate types of degassers such as vacuum degassers, filter based degassers and others.

In the apparatus of the disclosure the high pressure pump can be of any known type capable of maintaining flow rates through an aerosolizer and generating high back pressures or producing a high pressure fluid at a flow rate sufficient to form an aerosol. One example of a high pressure pump is a high pressure liquid chromatography (HPLC) pump capable of producing fluid flow rates of about 16 mL per minute at a fluid pressure of at least about 3,000 pounds per square inch. The Waters Model 590 HPLC pump (Waters Corp., Milford, Mass.) is an example of such a such high pressure pump. Those of ordinary skill in the art will recognize other high pressure pumps. The desired flow rates and fluid pressures can also be achieved by operating two or more pumps, such as Waters Model 515 pumps, in parallel, or by using upgrade kits to improve flow rates.

Many other different types of high pressure pumps are also known in the art. Those of ordinary skill in the art will recognize, for example, that these different types of high pressure pumps may include reciprocating pumps, rotary pumps, lobe pumps, centrifugal pumps, diaphragm pumps and peristaltic pumps with the caveat that the pump materials must not contaminate, or be contaminated, by the fluid being pumped.

In a typical reciprocating pump the back-and-forth motion of pistons inside of cylinders, typically coupled with appropriate check valves, provides the flow of fluid. Reciprocating pumps operate on the positive principle, that is, each stroke delivers a definite volume of liquid to the system. Several types of pumps, such as the radial piston and axial piston, are also classified as reciprocating pumps. These pumps are sometimes classified as rotary pumps, because a rotary motion is imparted to the pumps by the source of power. However, the actual pumping is typically performed by sets of pistons reciprocating inside sets of cylinders. High pressure pumps for HPLC are typically high volume, reciprocating pumps. Appropriate reciprocating pumps are available from Waters Corp., Scientific Systems, Inc. (State College, Pa.) and Idex, .nc./Sapphire Engineering, Inc. Idex pumps are positive displacement pumps. In a positive displacement pump, the piston position in the cylinder may be controlled by an optical encoder. Thus, an entire aerosol dose, such as 250 μL, can be delivered in one "shot" and the cylinder is then reloaded for the next delivery. There is no pulsation. It is preferred such pumps are capable of producing fluid flow rates of about 16 mL/min at a fluid pressure of at least 3,000 pounds per squire inch.

All rotary pumps have rotating parts which trap the fluid at the inlet and force it through an outlet. Gears, screws, lobes, and vanes are commonly used to move the fluid. Rotary pumps are positive displacement pumps of the fixed displacement type. Rotary pumps are designed with very small clearances between rotating parts and stationary parts to minimize slippage from the outlet side back to the inlet side.

A lobe pump employs a lobed element or rotor for pushing liquid. There are generally only two or throe lobes on each rotor. The two lobed elements are rotated, one directly driven by the source of power, and the other through timing gears. As the elements rotate, liquid is trapped between two lobes of each rotor and the walls of the pump chamber and carried around from the suction side to the discharge side of the pump. As liquid leaves the suction chamber, the pressure in the suction chamber is lowered and additional liquid is forced into the chamber from the reservoir. The lobes are constructed so there is a continuous seal at the points where they meet at the center of the pump. The lobes of the pump are sometimes fitted with small vanes at the outer edge to improve the seal of the pump. The vanes are mechanically held in their slots, but with some freedom of movement. Centrifugal force keeps the vanes snug against the chamber and the other rotating members. Lobe pumps with rubber lobes, for example, have been used to process fluids containing suspended solids such as, particulates or soft masses.

Centrifugal pumps are classified into three categories: radial, axial, or mixed flow. Radial flow centrifugal pumps develop pressure wholly by centrifugal force. Axial flow centrifugal pumps develop pressure by the propelling or lifting action of the vanes of the impeller on the liquid. Mixed flow centrifugal pumps develop pressure partly by centrifugal force and partly by the lift of the vanes of the impeller on the liquid. The two main components of a centrifugal pump are the impeller and the volute. The impeller produces liquid velocity and the liquid to discharge through the volute chamber and out of the pump. A centrifugal pump impeller slings the liquid out of the volute. It does not cup the liquid.

Diaphragm pumps are positive displacement pumps using a single or double diaphragm arrangement to move fluids through a chamber. In double diaphragm pumps, as the diaphragms move forward, fluid fills the aft chamber while fluid exits from the forward chamber. When the diaphragms move to the aft position, fluid enters the forward chamber and exits the aft chamber. This process repeats itself resulting in a smooth positive flow.

Peristaltic pumps work on the principle of sequential narrowing of the diameter of a shaft or portion of tubing in order to move liquid along the length of the tubing. The fluid is totally contained within a tube or hose and does not come into contact with the pump. They have no seals, glands of valves. This means they are ideal for hygienic or sterile operation. Being true positive displacement, there is no slip or back flow.

In the apparatus of the disclosure the switching valve can be a three way valve, a four way valve or any similar valve structure, or arrangement of valves, that can be configured to transfer a fluid though at least one delivery outlet or at least one release outlet. A rotary valve is one example of a switching valve, shear-type valve, having two flat surfaces with a gasket in between and appropriate holes in the surfaces and parts so that valving is achieved when the two surfaces are moved relative to one another. A switching valve may be placed in a given configuration by hydraulic actuation, pneumatic actuation, manual actuation, solenoid actuation, motor actuation or combinations of these. A switching valve can also be activated manually, without an intervening controller, using a small handle or similar structure to switch between valve configurations. One example of a switching valve is an injection valve for HPLC such as the Idex Health and Science (Oak Harbor, Wash.) RHEODYNE™ model 7725 injection valve, the RHEODYNE™ model 7725i injection valve and the RHEODYNE™ model 9725 injection valve. The RHEODYNE™ model 7010 valve is another example of a switching valve. Those of ordinary skill in the art will recognize other examples of switching valves.

The switching valve also affects the quality of the spray emanating from the tip of an aerosolizer. This is because the quality of the spray (mass median diameter, cone angle) emanating from the tip of an aerosolizer is a direct function of the pressure of a liquid being sprayed. It is also preferred that the mean median mass diameter of the dispersed phase in the aerosol be in a range of about 8 μm to about 22 μm. This means that the build-up and decay of the pressure exerted by a fluid at the delivery outlet in fluid communication with a switching valve must occur very rapidly so the aerosol quality does not decay and result in a liquid stream or the formation of very large liquid drops. Thus, it is preferred that the switching valve be able to handle a cycle of pressure build up and decay, such as at the delivery outlet, that is very rapid and occurs, for example, at about 200 milliseconds to about 500 milliseconds. In particular, it is preferred that switching to transfer a fluid though either the delivery outlet or the release outlet is performed by the switching valve in about 200 to 500 milliseconds or less.

A switching valve may be coupled to an actuator and can be controlled electrically so that the open and closed positions of the valve can be regulated by a controller. In the "on" configuration of a switching valve, a high pressure fluid is released into the delivery outlet and directed into the aerosolizer. In the "off" configuration of a switching valve, a high pressure fluid is transferred from the release outlet into a restrictor and a fluid, with low pressure, is released.

In the apparatus of the disclosure, the aerosolizer may be sized for insertion into an opening in a patient body or for placement adjacent to a target tissue such as the lungs. Such an aerosolizer may comprise a generally elongated sleeve member which defines a first end and a second end and includes a longitudinally extending opening therethrough. The first end of the sleeve member is placed in fluid communication with the delivery outlet of the switching valve or the high pressure pump outlet. A generally elongated insert is also provided. The generally elongated insert defines a first end and a second end and is received within at least a portion of the longitudinally extending opening of the sleeve member. The insert includes an outer surface which has at least one substantially helical channel provided that surrounds its outer surface and extends from the first end to the second end. The substantially helical channel of the insert is adapted to pass the liquid material which is received by the sleeve member. A generally elongated body member is also included which is in connection with the sleeve member. The body member includes a cavity provided in its first end which terminates at an end wall which is adjacent its second end. The end wall is provided having an orifice therein for spraying the fluid which is received from the insert. This spraying permits liquids, solids, or mixtures of these to be released and entrained in a gas, such as air, to produce an aerosol. Examples of aerosolizers of this type are commercially available from Penn-Century, Inc. (Philadelphia, Pa.) and are also described in, for example, U.S. Pat. Nos. 5,579,758, 5,606,789, 5,594,987, 6,016,800, 6,029,657 and 6,041,775.

An aerosolizer may also comprise any orifice through which a liquid, such as droplets, are released and entrained in a gas to produce a liquid aerosol. An aerosolizer may also comprise an orifice through which a gas passes into a fluid to produce a liquid aerosol. An aerosolizer may comprise an orifice through which solids, such as particulates, are released and entrained in a gas to produce a solid aerosol. An aerosolizer may also comprise an orifice through which a gas passes into a solid, such as a collection of particulates or a friable substance, to produce a solid aerosol. Aerosolizers for forming solid aerosols may have a compartment containing solids, such as friable solids or particulates, connected to a conduit containing a fluid so that the solid can be incorporated into the fluid. Aerosolizers may also comprise elements, such as ultrasonic probe elements, that can generate liquid droplets or particulates, that are released and entrained in a gas to produce an aerosol. Alternatively, an aerosolizer may comprise heating and cooling elements that vaporize a liquid and then partially condense the liquid, or condense the liquid to form droplets that are released and entrained in a gas to produce a liquid aerosol. An aerosolizer may also comprise heating and cooling elements that vaporize a solid and then partially, or completely, condense the solid to form particulates that are released and entrained in a gas to produce a solid aerosol. An aerosolizer may also comprise combinations of structures that produce an aerosol. Those of ordinary skill in the art will also recognize other aerosolizer structures.

An aerosolizer may comprise an extension connected to the portion of the aerosolizer containing the orifice, or other opening through which an aerosol is released. Such an extension can facilitate the delivery of an aerosol to a target tissue. The extension may be constructed of different materials, such as rigid or flexible materials. For example, the extension may be constructed from any flexible material such as a laminate, fiber reinforced polymer, metal and metal alloy or combinations of these. The extension can be constructed from polymers or combinations of polymers such as, for example, a polyether ether ketone (PEEK), polytetrafluoroethylene (PTFE), fluorinated ethylene propylene, ethylene tetrafluoroethylene (ETFE) and the like. The extension may be a pipe, such as tubing, or other fittings, such as a ball joint, which contains an interior passage suitable for fluid communication. The extension may also be articulated to accommodate insertion into body cavities or openings such as, for example, the trachea or a surgical incision. In particular, the aerosolizer and/or extension may be inserted into a body cavity through an opening created by tracheostomy or tracheotomy such as, for example, a tracheal port. The aerosolizer and/or extension may also simply be inserted down the throat and into the trachea. The extension may also have any shape that facilitates the delivery of an aerosol to a target tissue. For example, the extension may have a rounded shape, a cup-like shape, a curved shaped or a bulbous shape to facilitate the placement of an aerosolizer adjacent to a target tissue and the delivery of aerosol. The extension may also be of a number of different lengths to facilitate delivery of aerosol. For example, an extension to facilitate delivery of aerosol to the nasal passages may have a shorter length than an extension to facilitate the delivery of an aerosol adjacent to the carina. The extension may also comprise at least one sensor such as, for example, temperature, pressure or humidity sensors. The aerosolizer and/or extension may also be inserted into body cavities or other opening through a port in and may be associated with a bronchoscope or other instrumentation.

FIG. 1 shows one embodiment of an apparatus of the disclosure. In this embodiment a reservoir 101 contains a fluid that exits the reservoir through the outlet channel 102 and then enters a low pressure pump inlet 103. The fluid then passes from the low pressure pump inlet 103 into a high pressure pump 104 and enters a high pressure pump outlet 105. The fluid then passes from the high pressure pump outlet 105 into a switching valve 106 having a delivery outlet 107 and a release outlet 108. The fluid flow from the switching valve 106 is regulated by a controller 113 which controls the configuration of the switching valve 106. When the switching valve 106 is configured to produce an aerosol, the fluid passes through, a delivery outlet 107 and into an aerosolizer 109 to produce an aerosol. A flexible connector 112, such as a coil, may be placed between the delivery outlet 107 and aerosolizer 109 such that fluid passing from the delivery outlet 107 enters the flexible connector 112 and then passes into the aerosolizer 109. When the switching valve 106 is configured not to produce an aerosol, the fluid passes through a release outlet 108 and enters a restrictor 110. The fluid is then, released and can enter an appropriate vessel or conduit. The apparatus of the disclosure is capable of delivering samples of any volume from about 250 µL, with the preferred total sample volumes being about 10 mL to about 20 mL. Delivery is preferably made in the form of discrete, timed aliquots chosen by the operator. It is preferred that the apparatus of the disclosure delivery aerosol volumes of about 10 mL to about 20 mL. The apparatus of the disclosure is also capable of delivering samples of any other volume including volumes of about 10 µl or greater. For example, volumes of about 10 µL or about 125 µL are desirable for delivery to both pulmonary tissues and non-pulmonary tissues in some patients.

Figures 2, 3, 4:
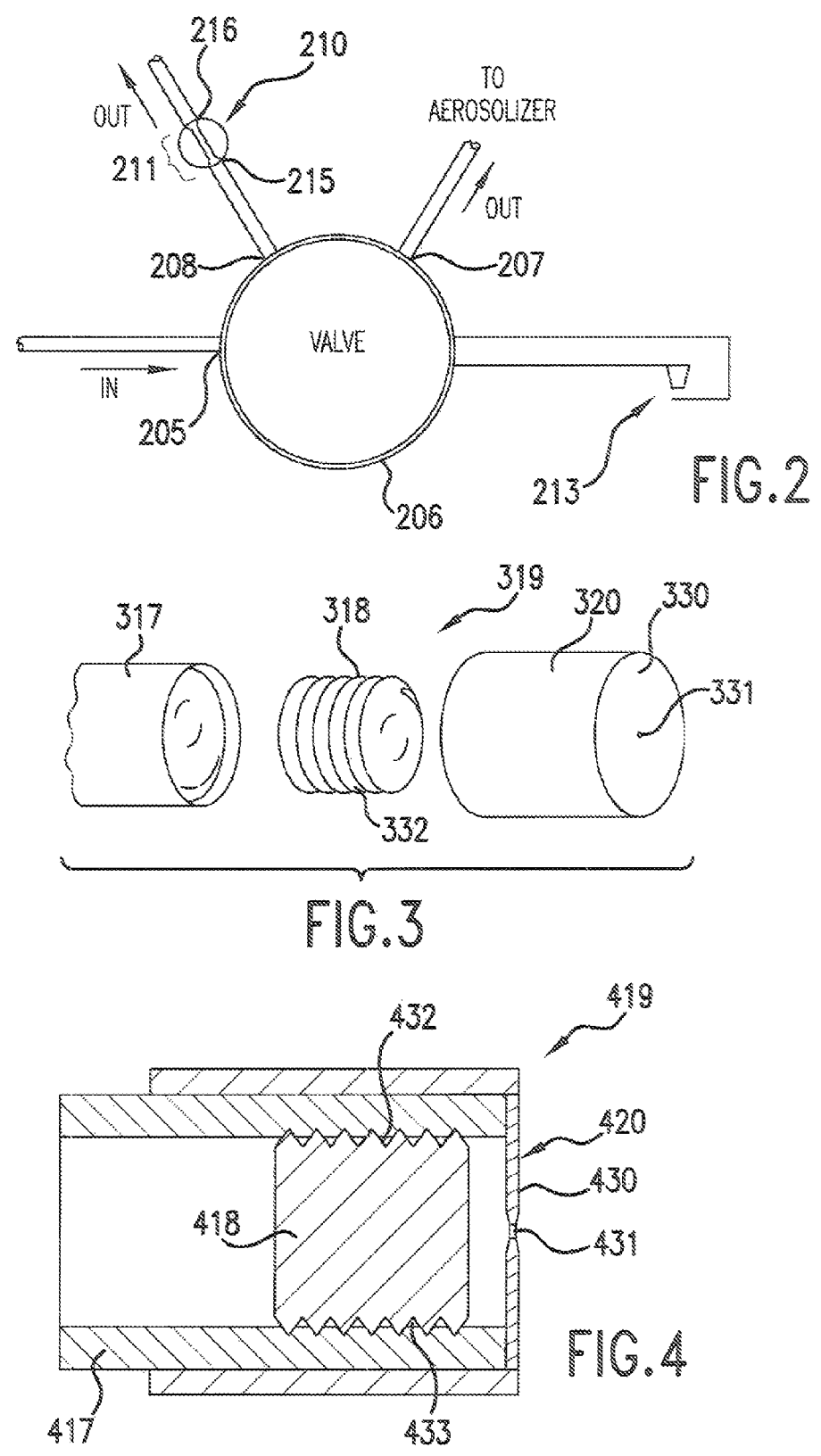

FIG. 2 shows one example of a switching valve. The switching valve 206 has a high pressure pump inlet 205, a delivery outlet 207 and a release outlet 208. The fluid flow from the switching valve 206 is regulated by a controller 213 which controls the configuration of the switching valve 206. When the switching valve 206 is configured to produce an aerosol, the fluid passes through a delivery outlet 207. When the switching valve 206 is configured not to produce an aerosol, the fluid passes through a release outlet 208 and enters a restrictor 210. The fluid is then released from the switching valve 206 and can then enter an appropriate vessel or conduit.

FIGS. 3 and 4 show one example of an aerosolizer. The MICROSPRAYER® Aerosolizer Model 1A-1B available from Penn-Century, Inc. (Philadelphia, Pa.) is an example of such an aerosolizer. The aerosolizer 319, 419 in this example comprises a body member 320, 420, as best seen in FIG. 3, that is comprised of a hollow tube member. A first end of the body member 320, 420 is provided with a cavity extending therein which terminates by an end wall 330, 430 provided adjacent its second end. In this example, the end wall 330, 430 is provided with an orifice 331, 431 extending through the length thereof. As best seen in FIG. 4, the configuration of the orifice 331, 431 in this example of an aerosolizer preferably includes a central area of substantially constant diameter and areas which are tapered or substantially conical-shaped at each end thereof. In alternative embodiments, the aerosolizer may have only one conical-shaped end and another end that is flat. Such alternative aerosolizer embodiments are described in, for example, U.S. Pat. No. 6,016,800. The MICROSPRAYER® Aerosolizer Model 1A-1C available from Penn-Century, Inc. (Philadelphia, Pa.) is an example of such an alternative aerosolizer embodiment. In this example of an aerosolizer, the body member 320, 420 is preferably comprised of 17-gauge extra-thin wall stainless steel tubing, which includes an outer diameter of 0.058 inches and an inner diameter of 0.050 inches. However, other suitable materials in any suitable configuration can be utilized for this same purpose.

In the example of an aerosolizer shown in FIG. 4, the insert 318, 418 is placed within the sleeve member 317, 417 and the sleeve member 317, 417 and body member 320, 420 are connected to each other to form the aerosolizer 319, 419. An aerosolizer can have the dimensions of a sub-miniature aerosolizer and be sufficiently small for intratracheal insertion, such as into an endotracheal tube, insertion into a bronchoscope, or insertion into the trachea directly. The aerosolizer of this example can be formed by providing a threaded channel 433 in the sleeve member 317, 417 that is tap formed in the inner surface. In an alternative embodiment of the aerosolizer, the tube end may be swaged with a hardened pin and the threaded insert secured with a small indentation. The end of the sleeve member 317, 417 is also preferably drilled to an inner diameter of 0.036 inches for a distance of 0.100 inches prior to providing the threaded channel 433, after which, the bored end is preferably tapped with a 1 mm×0.025 mm taper tap sufficient to provide a space of 0.020" length between the second end of insert 318, 418 and the second end of sleeve member 317. In the aerosolizer of this example, the threaded channel 433 is substantially helical and formed from threads 332, 432 on insert 318, 418.

Importantly, when used in conjunction with the Penn-Century MICROSPRAYER® Aerosolizer Model 1A-1C, or other aerosolizers, the disclosed apparatus is suitable for the on-demand delivery of liquid aliquots of any volume, as small as 250 µL, in the form of a relatively fine spray from the end of a long, thin tube (e.g., 0.025" diameter). It is also preferred that the aerosolizer be suitable for the delivery of total volumes of aerosol from about 10 mL to about 20 mL. The aerosolizer may also be suitable for delivering samples of any other volume including volumes of about 10 µL or greater. For example, volumes of about 10 µL or about 125 µL are desirable for delivery to both pulmonary tissues and non-pulmonary tissues in some patients. The tip resistance of the 1A-1C aerosolizer is such that a flow of 16.2 mL/min (270 µL/sec) generates a back pressure of about 3,000 psi and results in a spray with a particle size distribution of 8-22 µm (mass median diameter). The volume of liquid delivered per aliquot depends upon the length of time the system is maintained in an aerosol delivery configuration and the total delivered volume ultimately depends only upon the size of the reservoir from which the sample is drawn.

In the apparatus of the disclosure, the restrictor may be a pipe, fitting or combinations of these which provide sufficient flow resistance so that pressure is maintained on the inlet side of the restrictor. One example of a restrictor is a pipe comprising an inlet side and an outlet side in which the cross-sectional area of the interior passage within the pipe is tapered so that the cross-sectional area of the interior passage on the inlet side is greater than the cross-sectional area of the interior passage on the outlet side of the pipe. Another example of a restrictor comprises an inlet having a first cross-sectional area, an outlet and a porous solid between the inlet and outlet that produces a second cross-sectional area in the porous solid that is smaller than the first cross-sectional area. In the apparatus of the disclosure, a restrictor may be in fluid communication with a vessel, such as the reservoir, or a waste vessel. Alternatively, a restrictor may deliver a fluid to a drain or a fluid distribution system such as a sewer system. A restrictor may also be in fluid communication with a release outlet return.

An example of a restrictor is shown in FIG. 2. A restrictor 210 is provided as a fitting with an inlet side 215 and outlet side 216 that comprises a portion of interior passage 211 that is 2.5 inches in length with a substantially circular cross-section and a diameter of 0.005 inches. The flow resistance of the restrictor can be "tuned" by adjusting the length. Stated differently, the resistance of the restrictor can be matched to the resistance of the aerosolizer by adjusting the length of the restrictor.

High pressure back pressure regulator No. P-880 from Upchurch Scientific (Oak Harbor, Wash.) is another example of a restrictor and is adjustable between 2,000 and 5,000 psi.

One embodiment of the disclosure is an apparatus, wherein the switching valve contains a fluid at high pressure and the restrictor maintains the fluid at high pressure in the switching valve when the switching valve delivers the fluid to the release outlet.

Another embodiment of the disclosure is an apparatus, wherein the restrictor comprises an interior passage of 2.5 inches in length with a substantially circular cross-section and a diameter of 0.005 inches.

Another embodiment of the disclosure is an apparatus, further comprising a flexible connector in fluid communication with the delivery outlet and the aerosolizer, said flexible connector connecting both the delivery outlet and the aerosolizer.

The flexible connector may be a pipe, such as tubing, or other fittings, such as a ball joint, which contains an interior passage suitable for fluid communication. The flexible connector can be constructed from any flexible material such as a laminate, fiber reinforced polymer, metal and metal alloy or combinations of these. The flexible connector can be constructed from polymers or combinations of polymers such as, for example, a polyether ether ketone (PEEK), polytetrafluoroethylene (PTFE), fluorinated ethylene propylene, ethylene tetrafluoroethylene (ETFE) and the like. The flexible connector can have any geometry such as a coil, zig-zag and the like suitable for the extension, placement and retraction of a connected aerosolizer. Coil configurations may contain circular coils of varying diameters, number of coils and lengths of substantially linear tails. A helical coil is one example of such a coil configuration. Ideally, the flexible connector is suitable for non-contaminating fluid communication.

It is preferred that the flexible connector be constructed from tubing made of a polymer, such as PEEK, have a 1/16 inch outside diameter and an interior passage with a substantially circular cross section and a 0.02 inch inside diameter.

Another embodiment of the disclosure is an apparatus, wherein the flexible connector comprises a coil.

Another embodiment of the disclosure is an apparatus, wherein the flexible connector comprises a polyether ether ketone.

Another embodiment of the disclosure is an apparatus, wherein the switching valve is connected to a controller.

Another embodiment of the disclosure is an apparatus, wherein the controller is programmed to open the switching valve for a pre-set time interval.

Examples of controllers include personal computers, programmable logic controllers, circuits, switches, computer chips and combinations of these. A controller can also regulate the pressure, fluid flow and temperature of fluids in a switching valve to modulate the formation of liquid aerosols. A controller may affect the operation of a switching valve and the formation of liquid aerosols by feedback type control, feedforward type control or a combination of these control types. A controller may also utilize fuzzy logic to affect the operation of a switching valve.

The controller can comprise an electrical, or mechanical switch, such as a foot activated switch or a simple finger activated switch. The switch may be a push button switch conveniently located next to the aerosolizer. Other switch configurations may be used as well including lever type switches. The switch can provide momentary activation, sustained activation (e.g., push-on) and cut off activation (e.g., push-off) of the aerosol. The controller may also comprise at least one sensor that can monitor parameters such as pressure, fluid flow, humidity, temperature, the optical density or absorption of a medium, such as a liquid aerosol, and the like. For example, the controller can also comprise a pressure sensor and can be activated by feedback from the pressure sensor. The pressure sensor can be placed in the trachea of a patient so that a liquid aerosol is delivered upon inhalation when the pressure in the trachea decreases. The controller may also comprise a timer so that the production, and administration, of a liquid aerosol may be coordinated with the inhalation phase of a patient's breathing cycle. The controller may also comprise a force transducer, which when located on or around a patient's thorax, produces a signal corresponding to the inhalation phase of a patient's breathing cycle. Such respiration sensors are commercially available and include the PASSPORT™ respiration sensor belt PS-2133 Respiration Rate (PASCO Scientific, Inc., Roseville, Calif.) as well as the respiration monitor belt available from Vernier Software & Technology (Beaverton, Oreg.) and others.

The controller may comprise a hand piece that can be configured so the aerosolizer is positioned to form an angle of about 90° (FIGS. 6 and 9), about 135° (FIGS. 7 and 10), about 180° (FIG. 8), or any other convenient angle, between a long axis of the hand piece and a long axis of an aerosolizer. The hand piece can also comprise a button switch, or other switch, connected to a controller by electrical leads. The electrical leads and switch can form a circuit in the controller and may control aerosol production by the apparatus. The button switch can be positioned to accommodate activation by a thumb or other finger as shown in FIGS. 6 to 9. The hand piece may also comprise a housing of rigid or flexible materials and the housing may be of any appropriate configuration, or shape, suitable for being held by hand.

FIGS. 6 to 9 show, from a side perspective, one embodiment of a controller of an apparatus of the disclosure. FIG. 10 shows, from a side perspective, a cross-section through a long axis of one embodiment of a controller of an apparatus of the disclosure. In these embodiments the controller of the apparatus comprises a housing 635, 735, 835, 935, 1035 defining an interior lumen as well as having a first end and a second end which define a long axis. A button switch 634, 734, 834, 934, 1034 is located proximal to the first end of the housing 635, 735, 835, 935, 1035 and an aerosolizer 609, 709, 809, 909, 1009 is also located proximal to the first end of the housing 635, 735, 835, 935, 1035 to form an appropriate angle with a long axis of the housing and a long axis of the aerosolizer. Thus, in these embodiments the button switch 634, 734, 834, 934, 1034 and the aerosolizer 609, 709, 809, 909, 1009 are proximally connected to the first end of the housing 635, 735, 835, 935, 1035. The aerosolizer 609, 709, 809, 909, 1009 is in fluid communication with a flexible connector 612, 712, 912. The aerosolizer 609, 709, 809, 909, 1009 and flexible connector 612, 712, 912 may be joined by a length of tubing located partially, or completely, within the housing and this tubing may exit the housing proximal to the second end of the housing 635, 735, 835, 935, 1035. The button switch 634, 734, 834, 934, 1034 is connected to a first electrical lead 636, 736, 936, 1036 and a second electrical lead 637, 737, 937, 1037 and the leads 636, 736, 936, 1036, 637, 737, 937, 1037 are connected to a controller such that the controller comprises the button switch 634, 734, 834, 934, 1034. The first electrical lead 636, 736, 936, 1036 and second electrical lead 637, 737, 937, 1037 may be located partially, or completely, within the housing 635, 735, 835, 935, 1035 and may exit the housing proximal to the second end of the housing 635, 735, 835, 935, 1035. If the tubing is straight, the electrical leads and the tubing can be bundled in a flexible package.

In the apparatus and methods of the disclosure the aerosols may be administered with, or without, being respired by a patient and aerosol administration is not dependent on the respiratory capacity, function or health of a patient. This means the apparatus and methods of the disclosure make it possible to safely deliver far greater volumes than would be feasible in patients with compromised lung function, can be used in populations that cannot use inhalers (i.e., infants, the elderly, patients in a coma or unconscious, etc.) and that the dispersed phase in an aerosol need not be in a respirable range (e.g., 1-5 μm) to get past the body's anatomical barriers because the disclosed apparatus is carrying the aerosol past such barriers.

The controller may also be programmed to open a switching valve, or activate a high pressure pump, for a pre-set period of time to regulate the formation of liquid aerosols. These pre-set periods of time may include any time interval, such as 200 ms. These periods of time may also be constant time intervals or combinations of time intervals. For example, in a controller comprising a button switch, the activation of the switch would send a signal to a controller programmed to open the switching valve, or activate a high pressure pump, for a pre-set period of time and the controller would then open the switching value, or high pressure pump, for the pre-set period of time. After the pre-set period of time has elapsed, the controller would close the switching valve or deactivate the high pressure pump. A timer is one example of such a controller. An example of such a programmable controller is the Omega Model No. PTC-15 timer (OMEGA Engineering, Inc., Stamford, Conn.).

Another embodiment of the disclosure is an apparatus, wherein the aerosolizer comprises a substantially helical channel.

Another embodiment of the disclosure is an apparatus, wherein the controller comprises a housing with a first end and both the aerosolizer and a switch are proximally connected to the first end of the housing.

Another embodiment of the disclosure is an apparatus, further comprising a flexible connector in fluid communication with the delivery outlet and the aerosolizer, said flexible connector connecting both the delivery outlet and the aerosolizer, and wherein the switch further comprises an electrical lead.

Another embodiment of the disclosure is an apparatus, wherein the reservoir comprises a gas inlet.

Another embodiment of the disclosure is an apparatus, wherein the reservoir further comprises a septum containing the outlet channel and the gas inlet.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve containing a fluid at high pressure and having a delivery outlet and a release outlet; a controller connected to the switching valve; a flexible connector in fluid communication with the delivery outlet; an aerosolizer in fluid communication with the flexible connector; and a restrictor in fluid communication with the release outlet.

Another embodiment of the disclosure is an apparatus, wherein the restrictor maintains the fluid at high pressure in the switching valve when the switching valve delivers the fluid to the release outlet.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; and an aerosolizer in fluid communication with the high pressure pump outlet.

Another embodiment of the disclosure is an apparatus, further comprising a flexible connector in fluid communication with the high pressure pump outlet and the aerosolizer, said flexible connector connecting both the high pressure pump outlet and the aerosolizer.

Another embodiment of the disclosure is an apparatus, wherein the high pressure pump is connected to a controller.

Another embodiment of the disclosure is an apparatus, wherein the controller is programmed to activate the high pressure pump for a pre-set time interval.

Another aspect of the disclosure is an apparatus, further comprising a flexible connector in fluid communication with the high pressure pump outlet and the aerosolizer, said flexible connector connecting both the high pressure pump outlet and the aerosolizer, and wherein the switch further comprises an electrical lead.

Another aspect of the disclosure is an apparatus comprising a reservoir in fluid communication with an outlet channel; a low pressure pump inlet in fluid communication with the outlet channel; a high pressure pump in fluid communication with the low pressure pump inlet; a high pressure pump outlet in fluid communication with the high pressure pump; a controller connected to the high pressure pump; a flexible connector in fluid communication with the high pressure pump outlet; and an aerosolizer in fluid communication with the flexible connector.

Figure 13:
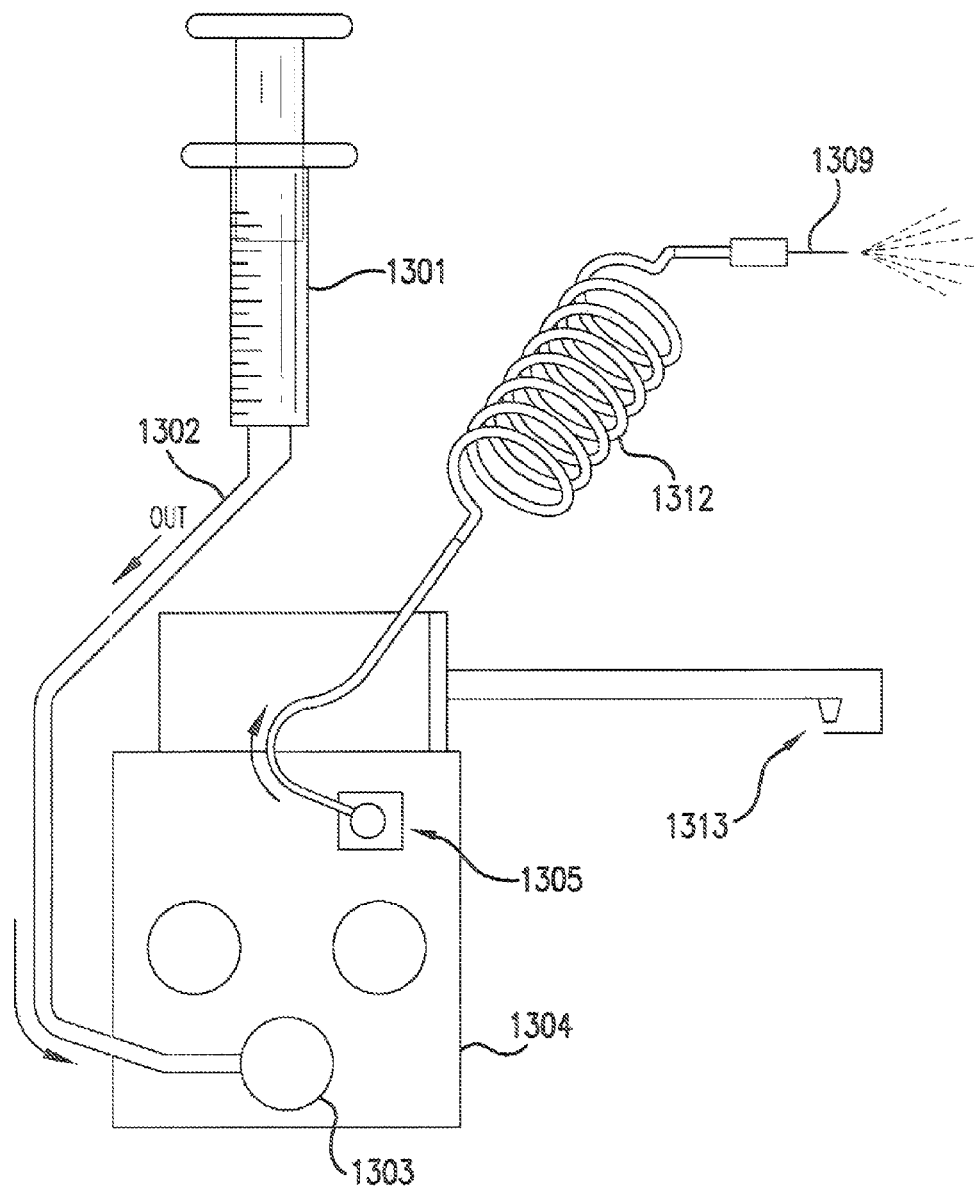
FIG. 13 shows, from a frontal perspective, one embodiment of an apparatus of the disclosure.

FIG. 13 shows one embodiment of an apparatus of the disclosure. In this embodiment a reservoir 1301 contains a fluid that exits the reservoir through the outlet channel 1302 and then enters a low pressure pump inlet 1303. The fluid then passes from the low pressure pump inlet 1303 into a high pressure pump 1304 and enters a high pressure pump outlet 1305. The fluid then passes from the high pressure pump outlet 1304 into an aerosolizer 1309 to produce an aerosol when the high pressure pump 1304 is operated. A flexible connector 1312, such as a coil, may be placed between the high pressure pump outlet 1305 and aerosolizer 1309 such that fluid passing from the high pressure pump outlet 1305 enters the flexible connector 1312 and then passes into the aerosolizer 1309. The apparatus of the disclosure is capable of delivering samples of any volume from about 250 μL, with the preferred total sample volumes being about 10 mL to about 20 mL. Delivery is preferably made in the form of discrete, timed aliquots chosen by the operator or is regulated by a controller 1313 programmed to activate the high pressure pump for a pre-set time interval. The controller may be activated by an operator controlled switch or automation activated such as by a sensor. The apparatus of the disclosure is also capable of delivering samples of any other volume including volumes of about 10 μL or greater. For example, volumes of about 10 μL or about 125 μL are desirable for delivery to both pulmonary tissues and non-pulmonary tissues in some patients.

Another aspect of the disclosure is an apparatus comprising a reservoir in fluid communication with an outlet channel and a release outlet return; a low pressure pump inlet in fluid communication with the outlet channel; a high pressure pump in fluid communication with the low pressure pump inlet; a high pressure pump outlet in fluid communication with the high pressure pump; a switching valve in fluid communication with the high pressure pump outlet, said switching valve containing a fluid at high pressure and having a delivery outlet and a release outlet; a controller connected to the switching valve; a flexible connector in fluid communication with the delivery outlet; an aerosolizer in fluid communication with the flexible connector; and a restrictor in fluid communication with the release outlet and the release outlet return and that maintains the fluid at high pressure in the switching valve.

Figure 5:
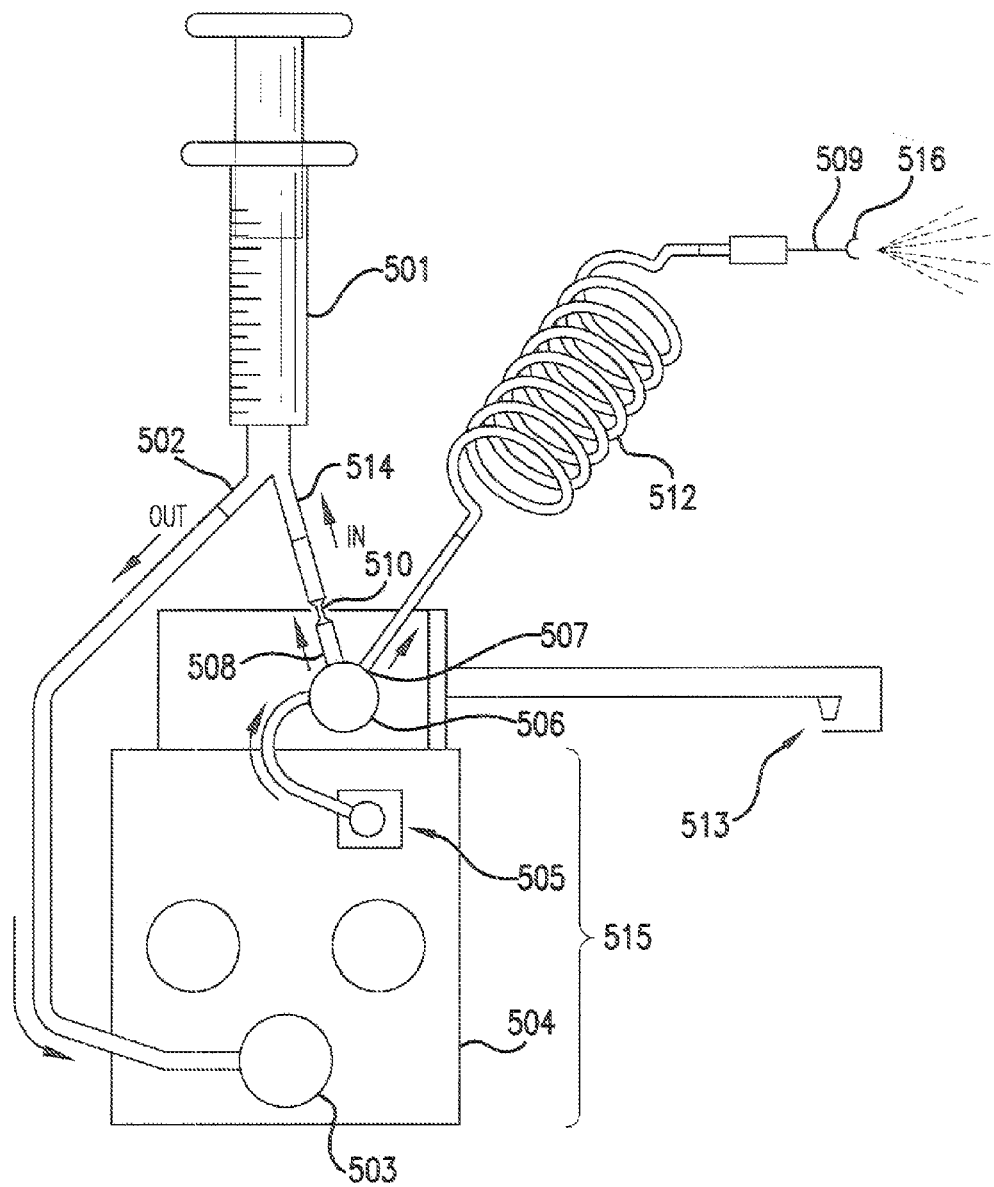
FIG. 5 shows, from a frontal perspective, one embodiment of an apparatus of the disclosure.
Figure 6:
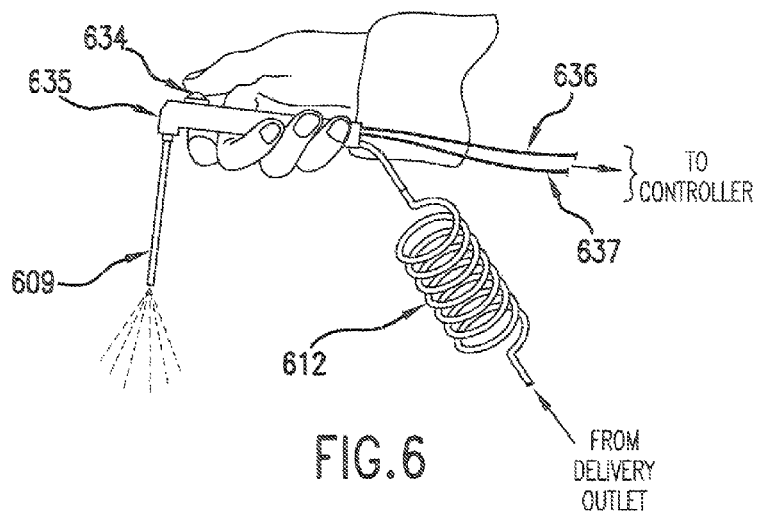
FIG. 6 shows, from a side perspective, one embodiment of a controller of an apparatus of the disclosure.
Figure 7:
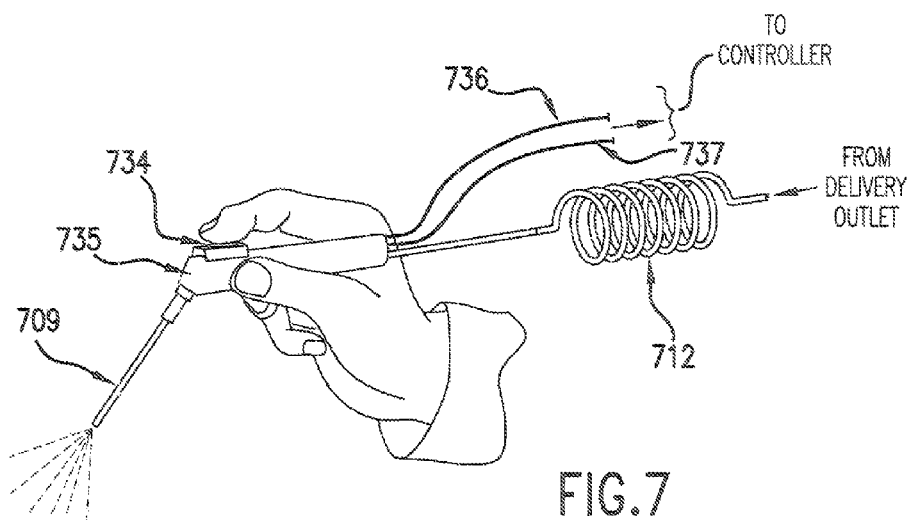
FIG. 7 shows, from a side perspective, one embodiment of a controller of an apparatus of the disclosure.

FIG. 5 shows another embodiment of an apparatus of the disclosure. In this embodiment a reservoir 501 contains a fluid that exits the reservoir through the outlet channel 502 and then enters a pressure generator 515. In particular, the fluid enters a low pressure pump inlet 503. The fluid then passes from the low pressure pump inlet 503 into a high pressure pump 504 and enters a high pressure pump outlet 505. The fluid then passes from the high pressure pump outlet 505 into a switching valve 506 having a delivery outlet 507 and a release outlet 508. The fluid flow from the switching valve 506 is regulated by a controller 513 which controls the configuration of the switching valve 506. When the switching valve 506 is configured to produce an aerosol the fluid passes through a delivery outlet 507 and into a aerosolizer 509 to produce an aerosol. In this embodiment, an extension 516 is connected to the aerosolizer 509. A flexible connector 512, such as a coil, may be placed between the delivery outlet 507 and aerosolizer 509 such that fluid passing from the delivery outlet 507 enters the flexible connector 512 and then passes into the aerosolizer 509. When the switching valve 506 is configured not to produce an aerosol, the fluid passes through a release outlet 508 and enters a restrictor 510. The fluid then enters a release outlet return 514 on the reservoir 501 so that the fluid released can enter the reservoir 501.

The release outlet return may be a fitting, pipe or armature which comprises an interior passage, or opening, located on the reservoir through which a fluid can be transferred, directly or indirectly, into the reservoir.

Another embodiment of the disclosure is an apparatus, wherein the restrictor comprises an interior passage of 2.5 inches in length with a substantially circular cross-section and a diameter of 0.005 inches, and the flexible connector is a coil comprising a polyether ether ketone.

Another embodiment of the disclosure is an apparatus, wherein the switch further comprises an electrical lead.

Another aspect of the disclosure is a method of administering an aerosol to a patient comprising providing an apparatus of the disclosure; placing the aerosolizer adjacent to a target tissue in a patient; and operating the apparatus to produce an aerosol; whereby an aerosol is administered to the patient.

In the methods of the disclosure, the aerosolizer can be placed adjacent to any target tissue in a patient. This may be accomplished by placing the aerosolizer adjacent to any external part of a patient's body such as the skin, eyes, and the like. This may also be accomplished by inserting the aerosolizer into an opening in a patient's body. Such openings may be naturally occurring or created by minimally invasive or invasive procedures. Examples, of such procedures include tracheotomy, tracheostomy, minitracheotomy, minitracheostomy, scopic procedures, and open surgical procedures. In some instances, it may be necessary to provide an environment containing a continuous, gaseous medium adjacent to a tissue. This facilitates aerosol formation by providing a sufficient amount of a gaseous medium to permit a liquid, such as fluid droplets, or a solid, such as a particulate, to be entrained in a gaseous phase so an aerosol can be formed. Such environments may be created, or maintained, within a body cavity or organ by gentle inflation of the organ or body cavity with a gaseous medium. Such environments may also be localized to a particular area by the use of rigid or flexible materials, such as adhesive films or partially open vessels, to define and limit the delivery of an aerosol to a particular area. An aerosolizer can also be placed adjacent to a target tissue, such as that in the lungs, by insertion into a cavity or passage, such as the trachea, which is connected to the target tissue.

Such approaches to placing an aerosolizer adjacent to a target tissue are also advantageous because they minimize the amount of aerosol delivered to non-target tissues. However, in some instances the target tissue may be one that facilitates the delivery of a component of an aerosol to a distal active site. For example, delivery of aerosols to the lungs may result in the delivery of an aerosol component to the blood stream.

Similarly, delivery of aerosols to nervous tissue may result in retrograde transport or anterograde transport of an aerosol component to a distal active site.

In the method of the disclosure, the target tissue may be any tissue in a patient's body. For example, such tissues may be epithelial tissues, including mucus membranes associated with body cavities or organs. Such tissues may also be connective tissues, muscle tissue, and nervous tissue. Tissue within the respiratory tract, such as that in the lungs, is a specific example of a target tissue to which an aerosol can be administered.

In the methods of the disclosure, an aerosol is administered to a patient. A patient may have any condition requiring the administration of an aerosol. Such conditions include those produced by cancers, trauma, infection, pain, genetic disorders, hyperthermia, dehydration, hypothermia and xenobiotics. Such conditions may also include tumors (such as non-malignant tumors) and hyperplasia.

The aerosol in the method of the disclosure may comprise a liquid as the dispersed phase. The liquid in the aerosol is in the form of small droplets. These droplets may also contain solids, having a mass, or other physical characteristics compatible with the formation of a liquid aerosol. Examples, of such solids include, for example, particles comprising biodegradable matrices or other solid materials as well as crystals of pharmaceutically active agents. Such solids can facilitate the delivery or sustained release of pharmaceutical agents administered in an aerosol. The liquid in an aerosol may also be water, an aqueous solution containing ions, an aqueous solution containing vitamins, a buffered aqueous solution, or any other type of aqueous solution or suspension. Such liquids may be administered to patients with conditions such as, for example, dehydration and electrolytic imbalances. The liquid in an aerosol may also comprise a pharmaceutical agent such as, for example, a small organic molecule, peptide chains, antibodies, antibody fragments, polynucleotides or combinations of these. Other examples of agents that can be included in a liquid aerosol include, for example, antibiotics, anesthetics, bronchodilators, vaccines, anti-inflammatory agents, lipopolysaccharide, neutrophil elastase, inhibitors of neutrophil elastase, surfactants, radioisotopes, epinephrine, heparin, L-dopa, cells, COX-2 inhibitors, gene therapy agents, microparticles and nanoparticles.

The aerosol in the method of the disclosure may also comprise a solid as the dispersed phase. The solid in the aerosol may be in the form of a particulate or a friable material. The particulates may also contain a liquid, having a mass, or other physical characteristics compatible with the formation of an aerosol. Examples, of such solids include, for example, particles comprising biodegradable matrices or other solid materials as well as crystals of pharmaceutically active agents. Such solids may also contain a fluid such as a buffer or pharmaceutically active agent. Such solids can facilitate the delivery or sustained release of pharmaceutical agents administered in an aerosol. The solid in an aerosol may also comprise a pharmaceutical agent such as, for example, a small organic molecule, peptide chains, antibodies, antibody fragments, polynucleotides or combinations of these. Other examples of agents that can be included in a solid aerosol include, for example, antibiotics, anesthetics, bronchodilators, vaccines, anti-inflammatory agents, lipopolysaccharide, neutrophil elastase, inhibitors of neutrophil elastase, surfactants, radioisotopes, epinephrine, heparin, L-dopa, cells, COX-2 inhibitors, gene therapy agents, microparticles and nanoparticles.

The aerosol in the method of the disclosure also comprises a gas as the continuous phase. If other than ambient air, the continuous phase can comprise one, or more, gases delivered concomitantly with the dispersed phase. For example, the gas in the aerosol can comprise pure oxygen or other oxygen containing mixtures such as, for example, air. Aerosols comprising oxygen gas can be administered to patients with hypoxic conditions. Mixtures of gases in the aerosol may also be selected to alter the density of the continuous phase and facilitate the suspension of liquid droplets or increase the residence time of an aerosol delivered to a target tissue such as, for example, the lungs. Nitrogen gas is one example of a gas that may alter the density of the continuous phase or increase residence times of an aerosol in a target tissue. The gas in the aerosol may also comprise one, or more, pharmaceutically active agents. The gas may comprise alcohols, ethers or other molecules in the gaseous phase that are pharmaceutically active. For example, the gas may comprise ethanol, diethyl ether or nitrous oxide.

Examples of drugs that may be administered in aerosols to patients as well as associated diseases or other conditions are listed in Table 1.

TABLE 1

| Drug | Diseases |
| --- | --- |
| Anesthetics | Targeted, topical administration of local anesthetics to the nose or back of the throat prior to insertion of a nasogastric tube or bronchoscope to reduce pain, coughing and the gag reflex |
| Antibiotics (Tobramycin, Fosfomycin ciprofloxacin) | Pneumonia, bacterial infections secondary to mechanical ventilation, Cystic fibrosis (CF) and non-CF bronchiectasis, *Staphylococcus aureus*, Influenza, *Moraxella catarrhalis*, coliforms and multidrugresistant bacteria, *Pseudomonas aeruginosa*, COPD/Emphysema, Acute sinusitis |
| Anti-inflammatories | COPD/Emphysema; Sarcoidosis, idiopathic pulmonary fibrosis, and autoimmune disease |
| Anti-fungal agents | Aspergillosis |
| Anti-rejection medications, Cyclosporin | Organ transplants |
| Anti-tuberculosis agents - vaccines and treatments | Tuberculosis |
| Bronchodilators, corticosteriods | Acute asthma, cystic fibrosis, COPD/Emphysema, smoke-related injury or inhalation, acute allergies |
| Chemotherapeutics | Lung cancer, diffuse adenocarcinoma |
| COX-2 inhibitors | — |
| Diagnostic materials and radio-opaque tracers | Imaging of lung surface or surface of bladder, colon, vagina, sinuses. |
| Emergency/Emergency MedicalTechnologies | — |
| Epinephrine | Allergies |
| Gene therapies, including viral, non-viral and lentiviral vectors | Cystic fibrosis, pulmonary hypertension |
| Heparin | Pulmonary embolism |
| L-dopa | — |
| micro- and nanoparticles formulations | — |
| monoclonal antibodies | — |
| peptides | — |
| proteins | — |
| Radiologic imaging | Administration of radio-opaque materials for assessment and diagnosis of organs and cavities |
| siRNA and DNA | influenza, cancer, tuberculosis, gene therapy, etc. |
| Stem cells | — |
| Surfactant (artificial or animal-derived) | Infant Respiratory Distress Syndrome, Adult Respiratory Distress Syndrome |

Table 2 also lists other conditions, or situations, where aerosol administration to a patient with the apparatus or methods of the disclosure may be desirable.

TABLE 2

| |
|---|
| Acute coronary syndrome |
| Acute lung injury |
| Acute myocardial infarction |
| Acute respiratory distress syndrome (ARDS) |
| Acute sinusitus |
| Administration of hormones |
| Allergic rhinitis |
| Anthrax |
| Arterial thrombosis |
| Asbestosis |
| Aspergillosis |
| Asthma |
| Atelectasis |
| Atopic dermatitis |
| Bacterial infection |
| Bacterial respiratory diseases |
| Biological warfare agents |
| Bleaomycin-induced lung injury |
| Brain cancer |
| Brain injury |
| Breast cancer |
| Cancer |
| Chronic Obstructive Pulmonary Disease (COPD) |
| Crohn's disease |
| Cystic Fibrosis |
| Diabetes |
| Diptheria |
| Diseases of the central nervous system |
| Drug delivery across pulmonary, oral, nasal, gastric, pulmonary, vaginal and other mucosal barriers |
| Drug delivery method validation |
| *E. coli* - bacterial infection |
| Emphysema |
| Endometriosis |
| Exposure to biological warfare agents |
| Fibroids |
| Gene therapy |
| Grave's Disease |
| Hearing loss |
| Heart failure |
| Hepatitis virus infection |
| Human papilloma virus infection |
| Hypoxic pulmonary vasoconstriction |
| Immune response |
| Influenza |
| Inhalation toxicology studies |
| Interstitial lung disease (ILD): including. Sarcoidosis, idiopathic pulmonary fibrosis, and autoimmune disease |
| Intraocular pressure relief |
| Lipid/DNA complexes |
| Lung cancer |
| Lung inflammation |
| Lung injury |
| Mannitol aerosols |
| Marek's disease |
| Measles |
| Monkeypox |
| Nanoparticle delivery |
| Neutrophilia |
| Nuclear or plutonium accident exposure |
| Orthopoxvirus (variola, monkeypox, vaccinia, buffalopox, and cowpox (CPV viruses) |
| Osteoporosis |
| Pain relief |
| Parkinson's Disease |
| Pediatric respiratory distress syndrome |
| Pneumoconiosis |
| Pneumocystosis |
| Pneumonia |
| Pneumonic plague |
| Prostate cancer |
| Protective effects of oxidized phospholipids |
| *Pseudomonas aeruginosa* infection |
| Psoriasis |
| Pulmonary Arterial Hypertension (PAH) |

TABLE 2-continued

| |
|---|
| Pulmonary arteriovenous malformation |
| Pulmonary aspergillosis |
| Pulmonary edema |
| Pulmonary embolism |
| Pulmonary fibrosis |
| Pulmonary macromolecule delivery |
| Rheumatoid arthritis |
| Rheumatoid lung disease |
| Sexual dysfunction |
| *Staphylococcus aureus* |
| Stroke |
| Surfactant administration to the lung |
| Treatment of exposure to environmental pollutants |
| Tuberculosis |
| Ulcerative colitis |
| Vaccination |
| Ventilator-induced lung injury |
| Viral Infection |
| Viral respiratory diseases |

Table 3 also lists examples of compositions and other substances, such as organisms, which may be administered in an aerosol to a patient with the apparatus or methods of the disclosure.

TABLE 3

| Compounds |
|---|
| 5-lipoxygenase inhibitor |
| Albuterol sulfate |
| Antibiotic |
| Anti-cholines |
| Beclomethasone |
| Beclomethasone 17-monopropionate |
| Beclomethasone dipropionate |
| Betamethasone |
| Bleomycin |
| Budesonide |
| Calcitonin |
| Capreomcyin-sulfate |
| Capreomycin |
| Capsaicin |
| Cells |
| cGMP PDE-5 inhibitors |
| Chimeric virus envelopes |
| Chitosan |
| Ciprofloxacin |
| Ciprofloxacin betaine |
| Citric acid |
| Cortocosteroids |
| Curcumin-derived compounds |
| CUROSURF ™ |
| CXCR1/2 receptor antagonists |
| DADLE |
| D-Alanine |
| Deslorelin |
| Dexamethasone |
| Dextran |
| Diaminofluoromethylpyridine derivatives |
| Dichloromethylene diphosphonate |
| Dihydropyridinone derivatives |
| Dihydropyrimidone Multimers |
| Diphtheria toxoid |
| D-Leucine-Enkephalin |
| DNA |
| Epidermal Growth Factor |
| Epoxygenase inhibitors |
| Fluoroquinolones |
| Flurbiprofen |
| Fluticasone |
| Gemcitabine |
| Gene therapy vectors |
| Glucose |
| Growth hormone releasing factor analogues |
| Heparinoid GM 2000 |
| Hepatitis B vaccine |

TABLE 3-continued

| Compounds |
|---|
| H-MAP |
| Human Growth Hormone |
| Human papilloma virus vaccines |
| Hydraluronic acid |
| Iloprost |
| Immunoglobulins |
| India ink |
| Influenza vaccine |
| Inhibitors of cyclooxygenase-2 |
| Insulin microparticle compositions |
| Interfering RNAs |
| Interferon-alpha |
| Ipratroplum bromide particles |
| Lactose |
| L-dopa |
| Lidocaine |
| Lipocalins |
| LUTROL ™ |
| Mannitol |
| Marimastat |
| MDL 101-146 |
| Measles vaccine |
| Microparticles |
| Microspheres |
| MMP-12 (matrix metalloprotease 2) |
| Muscarinic receptor antagonist (MRA) |
| N-(3,5-Dichloro-1-oxido-4-pyridinyl)-8-methoxy-2-(trifluormethyl)-5-quinoline carboxamide |
| Nanoparticles |
| Neurophil elastase inhibitors |
| Neuroquinine receptor competitors |
| Neutrophia elastase inhibitor (ONO-6818) |
| Neutrophil elastase |
| Neutrophil elastase inhibitors |
| Nitrogen-containing tricyclic compounds |
| Nonionic amphiphilic block copolymers |
| Norepinephrine |
| Oncostatin M |
| Ovalbumin |
| Paclitaxel |
| Para-aminosalicyic acid |
| Parathyroid Hormone (PTH) |
| Penyl amine carboxylic acid compounds |
| Phosphodiesterase inhibitors |
| Phospholipids |
| Pirfenidone |
| Poly(ethyleneimine) |
| Polyethylene glycol |
| Polyethylene glycol/surfactant mixtures |
| Pranlukast hydrate |
| Prostaglandin D2 synthase |
| Proteasome inhibitor |
| Pyrazolo[3,4-Z>]pyridine compounds |
| Radioisotopes |
| Recombinant *Bacillus anthracis* protective antigen |
| Rifampicin |
| Roflumilast |
| Rolipram |
| RPL554 |
| RPL565 |
| Salbutamol |
| Saline |
| Salmeterol |
| SB 202235 |
| SB 207499 (AIRIFLO ™) |
| Sch527123 |
| SOLVOPLEX ™ |
| Spermined dextran |
| SURVANTA ™ |
| Technetium-99m |
| Tetanus toxoid |
| TH9507 |
| Thioredoxin |
| Trehalose esters |
| Trinitrobenzolsulfonic acid |
| Triple neurokinin receptor antagonist (TNRA) |
| Trobramycin |
| Trospium |
| Vaccines |
| Viral, lentiviral and non-viral vectors |
| Vitamin D receptor antagonists |
| Xenon-129 |
| Xinafoate salts of substituted 5-oxazol-2-yl-guinoline compounds |
| Δ9-Tetrahydrocannabinol |

The apparatus and methods of the disclosure can also be used to deliver anti-microbial agents such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. Such agents can be used, for example, to treat Tuberculosis, *Staphylococcus, Streptococcus*, yeast, *Serratia. E. coli*, and *Pseudomonas aeruginosa* infections.

The apparatus and methods can also be used to deliver agents such as short-acting $\beta_2$-agonists, long-acting $\beta_2$-agonists, anticholinergics, corticosteroids, systemic corticosteroids, mast cell stabilizers, leukotriene modifiers, methylxanthines, $\beta_2$-agonists, albuterol, levalbuterol, pirbuterol, artformoterol, formoterol, salmeterol, anticholinergics including ipratropium and tiotropium; corticosteroids including beclomethasone, budesonide, flunisolide, fluticasone, mometasone, triamcinolone, methyprednisolone, prednisolone, prednisone; leukotriene modifiers including montelukast, zafirlukast, and zileuton; mast cell stabilizers including cromolyn and nedocromil; methylxanthines including theophylline; combination drugs including ipratropium and albuterol, fluticasone and salmeterol, budesonide and formoterol; antihistamines including hydroxyzine, diphenhydramine, loratadine, cetirizine, and hydrocortisone; immune system modulating drugs including tacrolimus and pimecrolimus; cyclosporine; azathioprine; mycophenolatemofetil; inhibitors of matrix metallo proteases (MMPs) including inhibitors of MMP-9 and MMP-2, and combinations thereof.

The apparatus and methods can also be used to deliver agents such as ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, timidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof.

Another embodiment of the disclosure is a method, wherein the target tissue is located in at least one selected from the group consisting of the abdominal cavity, cranial cavity, gastrointestinal tract, paranasal sinus, pelvic cavity, reproductive tract, respiratory tract, thoracic cavity and spinal cavity.

Examples of target tissues in these body cavities include tissues of the nose, mouth, throat, ears, eyes, sinus cavities, lungs, stomach, colon, urethra, urinary bladder, uterus, vagina, fallopian tubes and ovaries. It is preferred that the aerosolizer, such as the 1A-1C aerosolizer, have a small diameter such as, for example, 0.64 mm which facilitates aerosol delivery to the cranial cavity, pelvic cavity or spinal cavity.

Another embodiment of the disclosure is a method, wherein the patient has at least one condition selected from the group consisting of asthma, cancer, chronic obstructive pulmonary disease, cystic fibrosis, dehydration, diabetes, a genetic disorder, hypoxia, infection, inflammatory disease, osteoporosis, pain, Parkinson's disease, respiratory distress syndrome, and trauma.

Another embodiment of the disclosure is a method, wherein the target tissue is located in the lungs.

Another embodiment of the disclosure is a method, wherein the aerosolizer is inserted into an opening in a patient body.

Another embodiment of the disclosure is a method, wherein the opening is an incision in a patient body.

Another aspect of the disclosure is a method of administering a chemotherapeutic aerosol to the lungs of a patient comprising providing an apparatus of the disclosure in which the reservoir contains a chemotherapeutic agent; placing the aerosolizer adjacent to a target tissue in the lungs of a patient; and operating the apparatus to produce a chemotherapeutic aerosol; whereby a chemotherapeutic aerosol is administered to the lungs of the patient.

In the methods of the disclosure, a chemotherapeutic aerosol may be administered. Such aerosols may comprise at least one chemotherapeutic agent. Such chemotherapeutic agents include pharmaceutical agents that kill rapidly dividing cancer cells and include antineoplastic agents. Such chemotherapeutic agents may comprise, for example, small organic molecules, peptide chains, antibodies, antibody fragments, nanoparticle formulations, siRNA formulations, polynucleotides or combinations of these. A chemotherapeutic agent placed in a fluid, such as a liquid, can be aerosolized to form a liquid aerosol that is a chemotherapeutic aerosol. Alternatively, a chemotherapeutic aerosol can be formed when a liquid is aerosolized into a gas comprising the continuous phase that contains a chemotherapeutic agent (such as bis-(2-chloroethyl) sulfide (g)). A chemotherapeutic aerosol may also be formed when a solid chemotherapeutic agent is provided as a particulate or friable material and aerosolized to form a solid aerosol. Combinations of these approaches to form chemotherapeutic aerosols may also be used.

Another embodiment of the disclosure is a method, wherein the chemotherapeutic agent is cisplatin. Thus, one example of a chemotherapeutic agent useful in the methods of the disclosure is cisplatin. Other examples, include protein bound paclitaxel preparations such as ABRAXANE™, taxol and gemcitibine.

Another embodiment of the disclosure is a method, wherein the aerosolizer is inserted into an incision in a patient body.

For example, extra long catheters can be inserted in an incision or other opening of a patient with the help of specialized equipment and positioning software to permit biopsies of far deeper locations than would otherwise be reachable. The disclosed apparatus and aerosolizer may be narrow enough to go to these deep locations via such extra long catheters and can also force a dose down a very long tube to saturate a lesion with a chemotherapeutic agent directly.

Another embodiment of the disclosure is a method of administering a chemotherapeutic aerosol to a patient comprising providing an apparatus of the disclosure; supplying a chemotherapeutic agent to the apparatus; placing the aerosolizer adjacent to a target tissue in the patient; and operating the apparatus to produce a chemotherapeutic aerosol; whereby a chemotherapeutic aerosol is administered to the patient.

Another aspect of the disclosure is an apparatus comprising a reservoir in fluid communication with a pressure generator; a flexible connection in fluid communication with the pressure generator; and an aerosolizer in fluid communication with the pressure generator.

Pumps are one example, of a pressure generator. A pressurized fluid tank is another example of a pressure generator. A propeller is another example of a pressure generator. A flexible bladder that has been either, internally or externally pressurized, is another example of a pressure generator. A pressure generator may also apply a vacuum to move a fluid. Those of ordinary skill in the art will readily recognize other pressure generators.

Another aspect of the disclosure is an apparatus comprising a reservoir in fluid communication with a pressure generator; an aerosolizer in fluid communication with the pressure generator; and an extension attached to the aerosolizer.

Another embodiment of the disclosure is an apparatus, wherein the extension comprises at least one selected from the group consisting of a laminate, a fiber reinforced polymer, a metal, a metal alloy and a polymer.

Another embodiment of the disclosure is an apparatus, wherein the extension comprises a polyether ether ketone.

Another embodiment of the disclosure is an apparatus, wherein the extension comprises a sensor.

Another aspect of the disclosure is a method of administering a chemotherapeutic aerosol to a patient comprising providing an apparatus of the disclosure; supplying a chemotherapeutic agent to the apparatus; placing an extension adjacent to a target tissue in the patient; and operating the apparatus to produce a chemotherapeutic aerosol; whereby a chemotherapeutic aerosol is administered to the patient.

Another embodiment of the disclosure is a method, wherein the extension is inserted into an opening in a patient body.

The apparatus and methods of the disclosure may also be used with dry powder sprayers to produce, or administer, solid aerosols to a target tissue or other surface. The methods of the disclosure may also be performed using any apparatus disclosed herein.

Although the apparatus and methods have been described in connection with specific forms thereof, it will be appreciated that a wide variety of equivalents may be substituted for the specified elements described herein without departing from the spirit and scope of this disclosure as described in the appended claims.

What is claimed is:

1. An apparatus comprising:
   a reservoir in fluid communication with an outlet channel;
   a low pressure pump-inlet in fluid communication with the outlet channel;
   a high pressure pump in fluid communication with the low pressure pump-inlet;
   a high pressure pump-outlet in fluid communication with the high pressure pump, the high pressure pump-outlet having a switching valve, said switching valve having a delivery outlet; and
   an aerosolizer in fluid communication with the delivery outlet, the aerosolizer comprising an elongated sleeve member with a proximal end and a distal end, containing at the distal end an insert having an outer surface with a substantially helical channel surrounding the outer surface, and an orifice at an end wall thereof;
   wherein the apparatus supplies no gas to aerosolize liquid, and wherein when the reservoir contains a liquid, pressurized liquid flowing from the outlet channel to the orifice is unexposed to gas until it exits the apparatus via the orifice, and said pressurized liquid passes through the helical channel and through the orifice, at which point said pressurized liquid is aerosolized as it encounters ambient air at a pressure lower than a pressure of the pressurized liquid.

2. The apparatus of claim 1, further comprising a flexible connector in fluid communication with the high pressure pump outlet and the aerosolizer, said flexible connector connecting both the high pressure pump outlet and the aerosolizer.

3. The apparatus of claim 2, wherein the flexible connector comprises a coil.

4. The apparatus of claim 2, wherein the flexible connector comprises polyether ether ketone.

5. The apparatus of claim 1, wherein the high pressure pump is connected to a controller.

6. The apparatus of claim 5, wherein the controller is programmed to activate the high pressure pump for a pre-set time interval.

7. The apparatus of claim 1, wherein:
   the reservoir comprises a vial sealed with a septum;
   the outlet channel comprises a needle piercing the septum; and
   the apparatus further comprises an inlet to admit a gas into the reservoir via the pierced septum, to compensate for a volume of fluid transferred out of the reservoir.

8. The apparatus of claim 1, further comprising the switching valve being in fluid communication with the high pressure pump outlet, the switching valve containing a fluid at high pressure and having a delivery outlet and a release outlet; and a restrictor in fluid communication with the release outlet.

9. The apparatus of claim 8, further comprising a controller connected to the switching valve.

10. The apparatus of claim 1, wherein liquid passing through the orifice is aerosolized after leaving the apparatus and is entrained in the ambient air.

11. The apparatus of claim 1, wherein said high pressure pump produces, at the orifice, a flow rate for the liquid of about 16 mL per minute at a fluid pressure of about 3000 pounds per square inch.

12. The apparatus of claim 1, wherein said aerosolizer has an outer diameter of about 0.025 inches.

13. The apparatus of claim 1, wherein said aerosolizer has a length sufficient to enable it to be placed adjacent to a target tissue so that the aerosolized liquid is administered to said target tissue.

14. The apparatus of claim 13, wherein said target tissue comprises lung tissue.

15. The apparatus of claim 1, further comprising a flexible connector coupled between said delivery outlet and said aerosolizer, and in fluid communication therebetween.

16. The apparatus of claim 1, further comprising a restrictor in fluid communication with a release outlet, wherein the switching valve contains the liquid at high pressure and the restrictor maintains the liquid at high pressure in the switching valve when the switching valve delivers the liquid to the release outlet.

17. The apparatus of claim 16, wherein the restrictor comprises an interior passage of 2.5 inches in length with a substantially circular cross-section and a diameter of 0.005 inches.

18. The apparatus of claim 1, further comprising a controller connected to the switching valve, wherein the controller controls the opening and closing of the switching valve.

19. The apparatus of claim 18, wherein said controller is a programmable controller that is programmed to open the switching valve for a pre-set time interval.

20. The apparatus of claim 10, wherein the liquid contains solids.

21. An apparatus comprising:
   a reservoir having an outlet channel;
   a pressure generator in fluid communication with the outlet channel; and
   an aerosolizer in fluid communication with a delivery outlet of the pressure generator, the aerosolizer comprising a sleeve member containing an insert having a substantially helical channel surrounding its outer surface, and having an orifice at an end wall thereof;
   wherein the apparatus supplies no gas to aerosolize liquid, and wherein when the reservoir contains a liquid, pressurized liquid flowing from the outlet channel to the orifice is unexposed to gas until it exits the apparatus via the orifice, and said pressurized liquid passes through the helical channel and through the orifice, at which point said pressurized liquid is aerosolized.

22. The apparatus of claim 21, wherein said pressure generator comprises a pump.

23. The apparatus of claim 21, wherein said pressure generator comprises a pressurized fluid tank.

24. The apparatus of claim 21, wherein said pressurized liquid aerosolizes as it passes through the orifice and, after it exits the orifice, encounters ambient gas at a pressure lower than a fluid pressure generated by said pressure generator.

* * * * *